(12) United States Patent
Jansen et al.

(10) Patent No.: US 10,138,217 B2
(45) Date of Patent: Nov. 27, 2018

(54) METHODS FOR EXTRACTING AND CONVERTING HEMICELLULOSE SUGARS

(71) Applicants: VIRDIA, INC., Raceland, LA (US); Susan Lawson, Bethel, ME (US)

(72) Inventors: Robert Jansen, Collinsville, IL (US); Noa Lapidot, Mevaseret Zion (IL); Bassem Hallac, Jerusalem (IL); James Alan Lawson, Ellsworth, ME (US); Lee Madsen, Manassas, VA (US); Brendon Stout, Burlington, NC (US); Adam Tyler Carden, Henderson, NC (US); Michael A Faison, Danville, VA (US); Philip Travisano, Danville, VA (US); Michael Zviely, Haifa (IL)

(73) Assignee: VIRDIA, INC., Raceland, LA (US)

( * ) Notice: Subject to any disclaimer, the term of this patent is extended or adjusted under 35 U.S.C. 154(b) by 36 days.

(21) Appl. No.: 14/908,458

(22) PCT Filed: Sep. 3, 2014

(86) PCT No.: PCT/US2014/053956
§ 371 (c)(1),
(2) Date: Jan. 28, 2016

(87) PCT Pub. No.: WO2015/034964
PCT Pub. Date: Mar. 12, 2015

(65) Prior Publication Data
US 2017/0210721 A1 Jul. 27, 2017

Related U.S. Application Data

(60) Provisional application No. 61/976,481, filed on Apr. 7, 2014, provisional application No. 61/873,292, filed on Sep. 3, 2013.

(51) Int. Cl.
| | |
|---|---|
| C07D 307/50 | (2006.01) |
| C13K 1/02 | (2006.01) |
| C08B 37/00 | (2006.01) |
| C08H 8/00 | (2010.01) |
| C13K 11/00 | (2006.01) |
| C13K 13/00 | (2006.01) |

(52) U.S. Cl.
CPC ........ C07D 307/50 (2013.01); C08B 37/0057 (2013.01); C08H 8/00 (2013.01); C13K 1/02 (2013.01); C13K 11/00 (2013.01); C13K 13/002 (2013.01)

(58) Field of Classification Search
CPC .................................................. C07D 307/50
See application file for complete search history.

(56) References Cited

U.S. PATENT DOCUMENTS

| | | | |
|---|---|---|---|
| 2,559,607 | A | 7/1951 | Dunning et al. |
| 3,151,139 | A | 9/1964 | Van Der Plas et al. |
| 4,470,851 | A | 11/1984 | Paszner et al. |
| 4,533,743 | A | 8/1985 | Medeiros |
| 7,465,791 | B1 | 12/2008 | Hallberg et al. |
| 8,524,924 | B2 | 9/2013 | Burket et al. |
| 8,524,925 | B2 | 9/2013 | Sabesan et al. |
| 2008/0057555 | A1 | 6/2008 | Nguyen |
| 2010/0048924 | A1 | 2/2010 | Kilambi |
| 2010/0069626 | A1 | 3/2010 | Kilambi |
| 2010/0124583 | A1* | 5/2010 | Medoff ................... A61K 8/97 426/2 |
| 2011/0137051 | A1 | 6/2011 | Reunanen et al. |
| 2011/0144359 | A1 | 6/2011 | Heide et al. |
| 2013/0172583 | A1* | 7/2013 | Corbin ................ C07D 307/48 549/489 |
| 2014/0011248 | A1 | 1/2014 | Medoff et al. |

FOREIGN PATENT DOCUMENTS

| | | |
|---|---|---|
| CN | 101381351 A | 3/2009 |
| CN | 101463021 A | 6/2009 |
| CN | 101381351 B | 5/2011 |
| CN | 102126765 A | 7/2011 |
| CN | 102603681 A | 7/2012 |
| CN | 102126765 B | 10/2012 |
| EP | 2513080 B1 | 7/2015 |
| JP | 2013-126967 A | 6/2013 |
| WO | WO 2009/134791 A2 | 11/2009 |
| WO | WO 2010/009343 A2 | 1/2010 |
| WO | WO 2010/009343 A3 | 1/2010 |
| WO | WO 2011/070602 A1 | 6/2011 |
| WO | WO 2011/161141 A1 | 12/2011 |
| WO | WO 2012/057625 A2 | 5/2012 |
| WO | WO 2012/084810 A1 | 6/2012 |
| WO | WO 2013/025564 A2 | 2/2013 |
| WO | WO 2013/053816 A1 | 4/2013 |
| WO | WO 2013/101999 A1 | 7/2013 |
| WO | WO 2013/166469 A2 | 11/2013 |
| WO | WO 2015/087248 A1 | 6/2015 |

OTHER PUBLICATIONS

European Search Report dated Apr. 6, 2017 for European Patent Application No. EP14842137.3.

Bozell. The Use of Renewable Feedstocks for the Production of Chemicals and Materials—A Brief Overview of Concepts. National Renewable Energy Laboratory, 1617 Cole Boulevard, Golden, CO 80401. 2010.

Choudhary, et al. Highly efficient aqueous oxidation of furfural to succinic acid using reusable heterogeneous acid catalyst with hydrogen peroxide. Chemistry Letters. 2012; 41(4):409-411.

International search report and written opinion dated Jan. 26, 2015 for PCT/US2014/053956.

(Continued)

*Primary Examiner* — Timothy R Rozof
(74) *Attorney, Agent, or Firm* — Wilson Sonsini Goodrich & Rosati

(57) ABSTRACT

The present disclosure relates to methods of producing hemicellulose and conversion products thereof from a biomass. Also provided are hemicellulose products and other conversion products thereof.

18 Claims, 8 Drawing Sheets

(56) References Cited

OTHER PUBLICATIONS

Kim, et al. Dehydration of D-xylose into furfural over H-zeolites. Korean Journal of Chemical Engineering. 2011; 28(3):710-716.

Lessard, et al. High Yield Conversion of Residual Pentoses into Furfural via Zeolite Catalysis and Catalytic Hydrogenation of Furfural to 2-Methylfuran. Topics in Catalysis. 2010; 53(15):1231-1234.

Singh, et al. Integrated process for production of xylose, furfural, and glucose from bagasse by two-step acid hydrolysis. Industrial & Engineering Chemistry Product research and Development. 1984; 23:257-262.

Wyman. Potential Synergies and Challenges in Refining Cellulosic Biomass to Fuels, Chemicals, and Power. Biotechnol. Prog. 2003; 19:254-262.

* cited by examiner

METHODS FOR EXTRACTING AND CONVERTING HEMICELLULOSE SUGARS

CROSS-REFERENCE

The present application is a National Stage Entry of PCT Application No. PCT/US2014/053956, filed Sep. 3, 2014, which claims priority to U.S. Provisional Application No. 61/873,292, filed on Sep. 3, 2013; and U.S. Provisional Application No. 61/976,481, filed on Apr. 7, 2014; each of which is incorporated herein by reference in its entirety.

INCORPORATION BY REFERENCE

All publications, patents, and patent applications mentioned in this specification are herein incorporated by reference to the same extent as if each individual publication, patent, or patent application was specifically and individually indicated to be incorporated by reference. PCT/US2013/039585 filed May 3, 2013, and PCT/US2013/068824 filed Nov. 6, 2013 are incorporated by reference.

FIELD OF THE INVENTION

The disclosure relates to processing of biomass materials containing lignin, cellulose and hemicellulose polymers to form hemicellulose sugars and further processing to form conversion products. The disclosure relates to hemicellulose sugars and conversion products.

SUMMARY OF THE INVENTION

Provided herein are systems for producing furfural wherein the system is configured to produce at least 1.0 tons of furfural for each 2.3 tons of hemicellulose sugars provided, wherein the hemicellulose sugars comprise at least 80% xylose (by weight) and wherein the system is configured for processing at least 1.1 tons of hemicellulose sugars per day.

In some embodiments, the hemicellulose sugars comprise at least 1, 2 or 3 different C6 sugars.

In some embodiments, each C6 sugar is selected from the group consisting of glucose, mannose, and galactose. In some embodiments, the hemicellulose sugars further comprise arabinose. In some embodiments, the C6 sugar is glucose. In some embodiments, the hemicellulose sugars are at least 90, 95, 99 or 99.9% xylose (wt/wt).

In some embodiments, the systems described herein are configured to produce at least 0.5 tons of furfural per day. In some embodiments, the systems are configured to generate less than 0.01 ton of organic solvent waste per day. In some embodiments, the systems are configured to generate less than 20 ton of aqueous waste per day.

In some embodiments, the systems comprise a reaction control unit configured to adjust temperature or reaction residence time in a reactor based on chemical composition of the hemicellulose sugars. In some embodiments, the reaction control unit adjusts temperature and reaction residence time when the hemicellulose sugars comprise one or more C6 sugars. In some embodiments, the systems comprise a heat exchanger or a reactor operably connected to the reaction control unit. In some embodiments, the heat exchanger or reactor is configured for heating contents to greater than 100, 120, 130, 140, 150, 160, 170, 180° C.

In some embodiments, the systems further comprise a dilution control unit that controls: (a) an amount or a concentration of an acid and a salt in an aqueous sugar stream; (b) a concentration of the hemicellulose sugar in the aqueous sugar stream, and (c) an amount of purge water released from the system. In some embodiments, the dilution control unit increases acid concentration when the hemicellulose sugars comprise one or more C6 sugars. In some embodiments, the dilution control unit adjusts the salt concentration in the dilution tank to about 5% (wt/wt). In some embodiments, the dilution control unit increases concentration of the hemicellulose sugars by evaporating water. In some embodiments, the dilution control unit decreases the concentration of the hemicellulose sugars by adding water to the hemicellulose sugars. In some embodiments, the water is a furfural depleted aqueous stream from a separation module of the system. In some embodiments, the dilution control unit adjusts the dilution of the hemicellulose sugars in the dilution tank to 2-10% or 4-8% (wt/wt). In some embodiments, the dilution control unit adjusts the dilution of the hemicellulose sugars in the dilution tank to about 6% (wt/wt). In some embodiments, the system comprises a dilution tank operably connected to the dilution control unit and a furfural-depleted aqueous stream from a separation module of the system. In some embodiments, the furfural-depleted aqueous stream comprises water, acid and salt. In some embodiments, an anion of the salt is a conjugate base of the acid.

In some embodiments, the system converts xylose at a conversion of greater than 50, 60, 70, 80, 90, 95, 99, or 99.5%. In some embodiments, the xylose converted is converted to furfural with a selectivity of greater than 50, 60, 70, 80, 85, 90, 95, 99, or 99.5%.

In some embodiments, the system converts arabinose at a conversion of greater than 30, 40, 50, 60, 70, 80, 90, 95, 99, or 99.5%. In some embodiments, the arabinose converted is converted to furfural with a selectivity of greater than 50, 60, 70, 80, 85, 90, 95, 99, or 99.5%.

In some embodiments, the system comprises an extraction module for extracting hydrophilic impurities from an organic phase solvent by contacting in a counter current mode with an aqueous phase comprising acid and salt.

In some embodiments, the system is configured to recycle at least 60, 65, 70, 75, 80, 85, 90, or 95% of the furfural-depleted aqueous solution.

In some embodiments, the system comprises a preheating unit for preheating an organic solvent and an output to transfer the organic solvent to a reactor.

In some embodiments, the system comprises a separation module, wherein the separation module is configured for separating furfural, an aqueous stream, and an organic solvent stream.

In some embodiments, the system comprises a solvent feed tank configured to preheat solvent separated by and exiting from a separation module.

In some embodiments, the system comprises a reactor configured to maintain a preheated solvent and an aqueous solution comprising hemicellulose sugars at a set temperature and pressure thereby converting xylose from the hemicellulose sugars into furfural.

In some embodiments, the system comprises a solvent feed tank, a dilution feed tank, a reactor downstream of the solvent feed tank and the dilution feed tank, and a separation module downstream of the reactor; wherein the separation module is configured for separating furfural, an aqueous stream, and an organic solvent stream; wherein (i) the solvent feed tank is configured to preheat solvent separated by and exiting from the separation module; (ii) the dilution feed tank is configured to dilute the hemicellulose sugars with the aqueous stream separated by and exiting from the separation module; and (iii) the reactor is configured to maintain the preheated solvent and the diluted hemicellulose sugars at a set temperature and pressure thereby converting xylose from the hemicellulose sugars into furfural. In some embodiments, the separation module comprises one or more distillation columns, for example, two or more extractors.

In some embodiments, the systems are operable on a continuous basis.

In some embodiments, the systems comprise at least 2 recycling loops. For example, an aqueous solution recycling loop and an organic solvent recycling loop. In some embodiments, the systems comprise at least 3 continuous loops. In some embodiments, at least 2 of the 3 continuous loops are organic solvent recycling loops.

In some embodiments of the systems described herein, the furfural is isolated as a substantially pure product. For example, the isolated furfural can be at least 70, 80, 90, 95, 99, or 99.9% pure.

In some embodiments, the system comprises a separation module for separating a reaction mixture into a furfural-enriched product stream, an aqueous stream and an organic solvent stream, wherein (i) the furfural-enriched product stream has a furfural purity of at least 90%; (ii) the aqueous stream comprises acid and less than 1% (wt/wt) organic solvent and less than 2% (wt/wt) hemicellulose sugars; and (iii) the organic solvent stream comprises an S5 solvent and less than 1% (wt/wt) non-S5 solvent impurities.

Further provided herein are processes comprising: (a) separating a biphasic reaction mixture comprising furfural to form a furfural-enriched organic stream and an intermediate aqueous stream; (b) removing at least a portion of the furfural from the furfural-enriched organic stream to produce an isolated furfural stream and a furfural-depleted organic stream; (c) contacting the intermediate aqueous stream with at least a portion of the furfural-depleted organic stream to produce a biphasic extraction mixture; (d) separating from the biphasic extraction mixture a furfural-depleted aqueous stream and an intermediate organic stream; and (e) reintroducing the intermediate organic stream into the furfural-enriched organic stream.

In some embodiments of the processes, at least a portion of the furfural-depleted organic stream is utilized to generate additional biphasic reaction mixture. In some embodiments, at least a portion of the furfural-depleted aqueous stream is utilized to dilute feedstock hemicellulose sugars to generate additional biphasic reaction mixture. In some embodiments at least a portion of the furfural-depleted aqueous stream is purged from the system. In some embodiments, at least a portion of the furfural-depleted organic stream is purified by base or water extraction. In some embodiments, the process further comprises converting isolated furfual from the isolated furfural stream to tetrahydrofuran (THF). In some embodiments, the organic stream comprises S5 solvent. In some embodiments, the process is a continuous loop. In some embodiments, at least 60%, 70%, 80%, or 90% of furfural in the first biphasic solution becomes isolated furfural.

Further provided herein are processes to produce furfural, comprising: (a) feeding a reactor with an aqueous sugar stream and an organic stream to form a biphasic reaction mixture; wherein the aqueous sugar stream comprises xylose, salt, and an acid; wherein the acid is at normality of 0.05 to 2; (b) heating the biphasic reaction mixture to convert at least a portion of the xylose to furfural; (c) separating the biphasic reaction mixture to produce a furfural-depleted organic stream, an isolated furfural stream, and a furfural-depleted aqueous stream; and (d) recycling at least a portion of the furfural-depleted organic stream to the feed of the reactor. In some embodiments, the process further comprises: (e) washing the furfural-depleted organic stream with water and separating the phases to form an aqueous waste stream and an extracted-return organic stream. In some embodiments, the process further comprises: (f) contacting a portion of the furfural-depleted organic stream with a basic aqueous stream of pH>10.0 to form a basic extraction mixture; and (g) separating the basic extraction mixture to obtain a purified-return organic stream and a basic aqueous waste stream comprising impurities. In some embodiments, the aqueous sugar stream comprises about 6% hemicellulose sugars (wt/wt). In some embodiments, the aqueous sugar stream comprises between about 70% and about 90% xylose (wt/wt, sugar dry solid basis). In some embodiments, the aqueous sugar stream further comprises between about 3% and about 15% arabinose (wt/wt, sugar dry solid basis). In some embodiments, the aqueous sugar stream comprises at least 1% and up to 20% C6 sugar relative to xylose (wt/wt). In some embodiments, the aqueous sugar stream further comprises less than 5000 ppm in total (wt relative to xylose wt) in said composition of elements; wherein said elements are Ca, Cu, Fe, Na, K, Mg, Mn, S and P, excluding the amounts of these elements contributed by the salt and acid. In some embodiments, the aqueous sugar stream comprises 5, 6, 7, 8 or 9 of the following characteristics: (i) a ratio of oligosaccharides to total dissolved sugars of not more than 0.10 weight/total sugar weight; (ii) a ratio of xylose to the total dissolved sugars of at least 0.50 weight/total sugar weight; (iii) a ratio of arabinose to total dissolved sugars of not more than 0.15 weight/total sugar weight; (iv) a ratio of galactose to total dissolved sugars of not more than 0.05 weight/total sugar weight; (v) a ratio of the sum of the glucose and fructose to total dissolved sugars of not more than 0.15 weight/weight; (vi) a ratio of mannose to total dissolved sugars of not more than 0.05 weight/weight; (vii) a ratio of fructose to total dissolved sugars of not more than 0.10 weight/weight; (viii) phenols in an amount of not more than 1000 ppm; (ix) hexanol in an amount of not more than 0.1% weight/weight: and (x) less than a total of 1000 ppm of the elements Ca, Cu, Fe, Na, K, Mg, Mn, S and P relative to total sugar dry solid, excluding the amount contributed by the acid and salt. In some embodiments, the ratio of oligosaccharides to total dissolved sugars is not more than 0.07. In some embodiments, the ratio of oligosaccharides to total dissolved sugars is not more than 0.05. In some embodiments, the ratio of xylose to total dissolved sugars is at least 0.40 weight/weight, for example, at least 0.70 weight/weight or at least 0.80 weight/weight. In some embodiments, the ratio of the sum of glucose and fructose to total dissolved sugars is not more than 0.09, for example, not more than 0.05. In some embodiments, the xylose-enriched stream hemicellulose sugar mixture comprises phenols in an amount up to 60 ppm, for example in an amount up to 0.05 ppm.

Also provided herein, are processes to produce furfural comprising: preheating an organic solvent to form a preheated organic stream; contacting the preheated organic stream with an aqueous sugar stream comprising xylose, an acid, and a salt to form a biphasic reaction mixture; heating the biphasic reaction mixture at a predetermined temperature for a predetermined time to convert at least a portion of the xylose to furfural. In some embodiments, the predetermined temperature or time is calculated based on the composition of the aqueous sugar stream. In some embodiments, the predetermined temperature is at least 170° C. In some embodiments, the predetermined time is 60 to 1800 seconds.

In some embodiments, the organic solvent is an S5 solvent, for example, tetralin. In some embodiments, the reactor is a continuously mixed reactor. In some embodiments, the pressure of the reaction is at least 1 bar pressure higher than the equivaltent saturated steam pressure of the reaction. In some embodiments, at least 80% of the xylose is converted to furfural (molar yield). In some embodiments, the process further comprises isolating the furfural. In some embodiments, the acid is HCl. In some embodiments, the salt comprises chloride. In some embodiments, the process further comprises conversion of the furfural to a conversion product, said conversion product comprises at least one member selected from the group consisting of, furfuryl alcohol, furan, tetrahydrofuran, succinic acid, maleic acid, furoic acid, and any combination thereof. In some embodiments, said conversion product is selected from the group consisting of furfuryl alcohol, furan, tetrahydrofuran, succinic acid, maleic acid, furoic acid, and any combination thereof.

Also provided herein, is a computer recordable medium comprising one or more inputs selected from the group consisting of identity of a sugar, a relative abundance of one or more sugars, a concentration of a sugar, the pH or a solution comprising a sugar, the temperature of a solution comprising a sugar; wherein the medium instructs a processor to calculate one or more reaction parameters selected from the group consisting of an effective reaction time, reaction temperature, or reaction pressure; and the medium operates one or more valves to obtain the one or more reaction parameters.

Further provided herein is a composition comprising: at least 90% furfural by weight; water in an amount up to 5% by weight; S5 solvent in amount up to 1% by weight; and at least two impurities, wherein the total amount of all impurities together is up to 5000 ppm by weight relative to furfural; wherein the impurities are selected from the group consisting of formic acid, levulinic acid, acetic acid, 5-chloromethylfuran-2-carbaldehyde, 5,5'-diformyl-2,2'-difuran, HMF, and HCl. In some embodiments, the composition comprises at least 95, 96, 97, 98, 99 or 99.9% furfural, wherein water amount is less than 1% and S5 amount is less than 0.1%. In some embodiments, the S5 solvent is tetralin. In some embodiments, the composition comprises HMF and 5,5'-diformyl-2,2'-difuran.

Also provided herein is a composition comprising: at least 95% tetralin by weight; at least two impurities, wherein the total amount of all impurities together is up to 2% by weight relative to tetralin; wherein the impurities are selected from the group consisting of furfural, water, HMF, HCl, NaCl, formic acid, levulinic acid, acetic acid, 5-chloromethylfuran-2-carbaldehyde, 5,5'-diformyl-2,2'-difuran,5-(furan-2-yl-hydroxy-methoxymethyl)-furan-2-carbaldehyde, humins, cis-decalin, trans-decalin, naphthalene, and polyfurfural species.

Additionally provided herein is a composition comprising: an aqueous solution comprising about 5% NaCl, 0.3-2% HCl, HMF, furfural, S5 solvent, xylose, arabinose, glucose, levulinic acid, and formic acid.

Also provided herein is a system for producing furfural wherein the system is configured to produce at least 1.0 tons of furfural for each 2.3 tons of hemicellulose sugars provided, wherein the hemicellulose sugars comprises arabinose and wherein the system is configured for processing at least 1.1 tons of hemicellulose sugars per day.

Additionally provided is a process for converting arabinose to furfural comprising: contacting arabinose with a pre-heated organic solvent stream to form a reaction mixture; allowing the reaction mixture to convert arabinose to furfural; separating furfural from an organic phase of the reaction mixture; diverting a remainder furfural-depleted organic stream back for preheating and contacting with additional arabinose. In some aspects, the process further comprises diverting an aqueous stream from the reaction mixture to a dilution tank for contacting with additional arabinose.

DETAILED DESCRIPTION OF THE INVENTION

The present disclosure relates to lignocellulosic biomass processing and refining to produce hemicellulose sugars, and their conversion to high-value products, such as furfural and THF. Lignocellulosic biomass can be processed and refined by any method known in the art. Furfural can be further converted in a myriad of reactions to high value acids, monomers and other chemical reagents and products.

Figure 1:
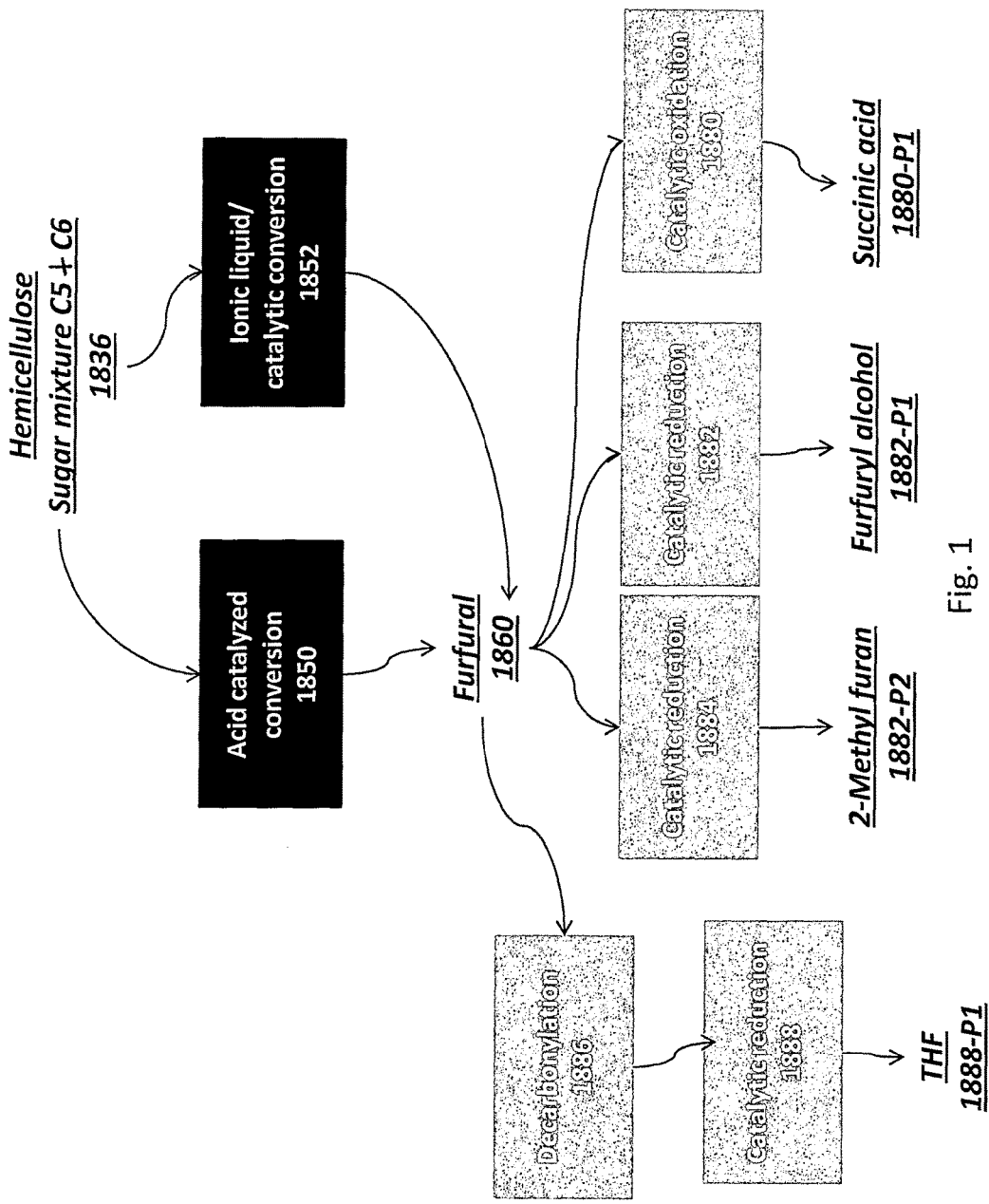
FIG. 1 shows a schematic representation of an exemplary method of conversion of a hemicellulose sugar mixture comprising C5 and C6 carbohydrates to downstream products.

A general scheme for the conversion of hemicellulose sugars to downstream products is shown in FIG. 1. Hemicellulose sugars can be converted to furfural via an acid-catalyzed conversion 1850 or an ionic liquid catalytic conversion 1852. Furfural is a versatile building block that can be transformed into a variety of high value organic compounds. Furfural can be decarbonylated and under a catalytic reduction 1888 to form tetrahydrofuran (THF). Furfural can be directly reduced via catalytic reduction 1884 to form 2-methyl furan. Under different reduction conditions, catalytic reduction 1882, furfural can form furfuryl alcohol. Alternatively, oxidation 1880 of furfural can lead to succinic acid. The diversity of downstream products showcases the value of furfural as an organic building block.

1. Conversion of Hemicellulose Sugars to Furfural

The present disclosure offers a viable approach to produce furfural from hemicellulose sugars and includes systems, methods, and processes to produce furfural from hemicellulose sugars.

System for Producing Furfural

Figure 2:
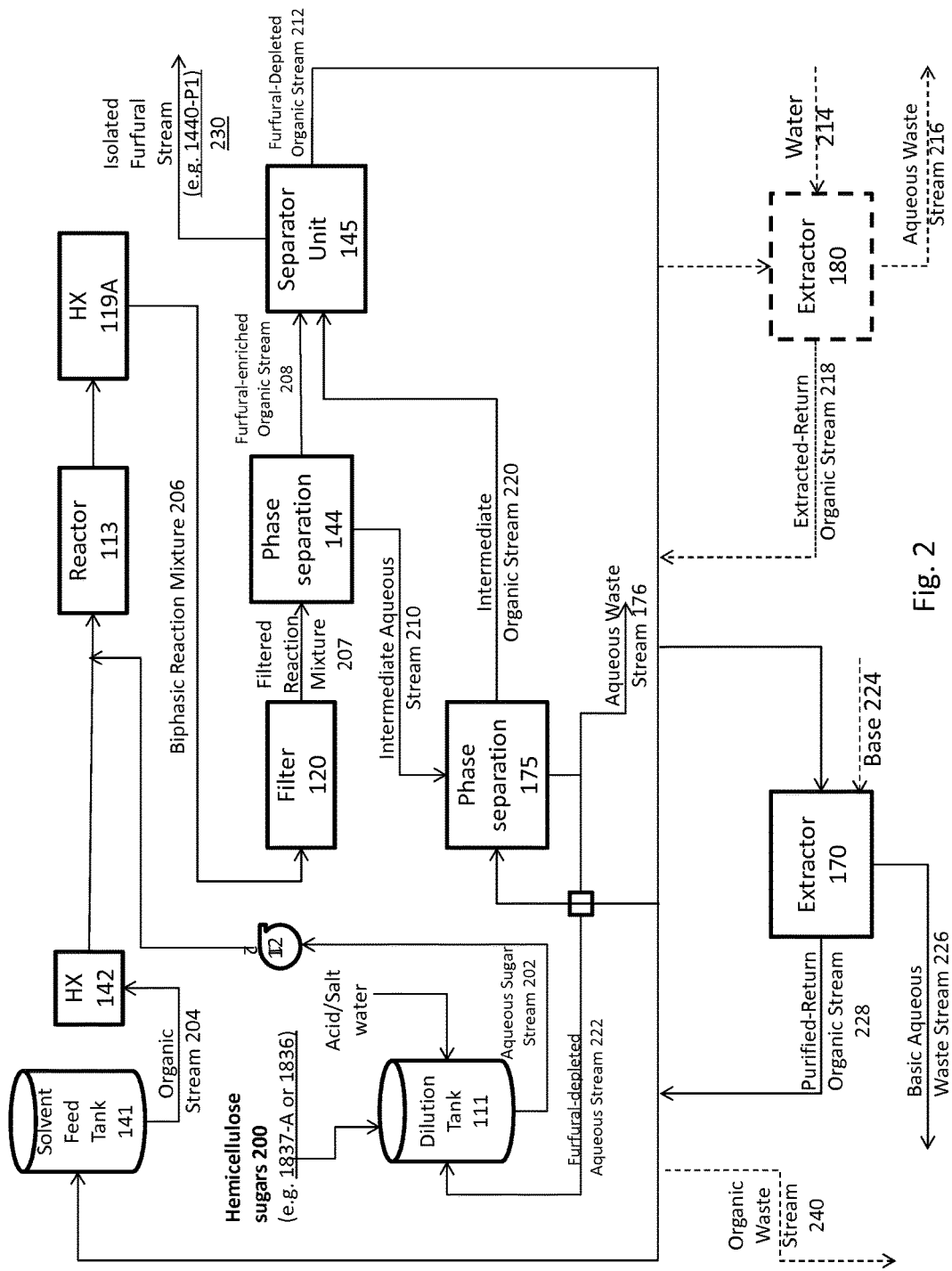
FIG. 2 shows a flow scheme for conversion of a hemicellulose sugar stream to a furfural stream.

A schematic diagram of a system for producing furfural is shown in FIG. 2. In general, the system of FIG. 2 converts hemicellulose sugars 200 to form an isolated furfural stream 230. The system has an input that incorporates hemicellulose sugars 200 into the system. As described herein, the hemicellulose sugars comprise at least one C5 sugar (e.g., xylose or arabinose). The hemicellulose sugars are added to dilution tank 111 either mechanically (if hemicellulose sugars 200 is a solid) or via an input valve (if the hemicellulose sugars are part of an aqueous solution). The input of hemicellulose sugars 200 to the dilution tank 111 can be batch wise or a constant flow.

The dilution tank 111 is also coupled to an input for adding an aqueous solution comprising water, a furfural-depleted aqueous stream 222, or a combination thereof. The dilution tank 111 is also optionally coupled to an acid reservoir and a salt reservoir. Preferably, the acid is a mineral acid (e.g., HCl or $H_2SO_4$), and the salt is selected to have the same anion with the acid. For example, when HCl is chosen as the acid a chloride salt is selected (e.g., NaCl or KCl), and when sulfuric acid is selected as the acid a sulfate salt is selected (e.g., $Na_2SO_4$). The hemicellulose sugars 200 are provided to the dilution tank 111 where they are contacted with at least some of the aqueous stream and additional acid and salt from the acid reservoir and salt reservoir.

The amount of reagents provided into a dilution tank is controlled by a dilution control unit. The dilution control unit is programmed to create a total hemicellulose sugar concentration in the range of 2-20% wt/wt, with a total acid concentration of 0.1-2% wt/wt, and a total concentration of salt in the range of 2.5-7.5%. The dilution control unit can include a computer (or a controller) configured to receive input on the following variables: identity and quantity of hemicellulose sugars 200, identity and quantity of residual hemicellulose sugars in furfural-depleted aqueous stream 222, identity and quantity of HMF and/or other byproducts in furfural depleted aqueous stream 222, amount and quantity of mineral acid and salt in dilution tank 111. The dilution control unit can use such variables to calculate the following: an amount of furfural-depleted aqueous stream 222 to expunge prior to entering dilution tank 111, an amount of furfural-depleted aqueous stream to add to dilution tank 111, amount of water to add to dilution tank 111, or an amount of water to remove from dilution tank 111 by evaporation. Such a computer is a specific computer that is also programmed to control the following processes in the system: valve opening or fluid flow from an acid or salt reservoir to dilution tank 111, valve opening or fluid flow of furfural-depleted organic stream 212 or water to dilution tank 111, control of an evaporator to remove water from hemicelluloses sugars feed 200, or control of an evaporator to remove water from dilution tank 111. In some instances, a dilution control unit can be pre-set at specific parameters for temperature, acid concentration or salt concentration and will operate a heating unit, acid reservoir input valve or flow modulator, salt reservoir input valve or flow modulator. The identity and relative amounts of hemicellulose sugars fed into the dilution tank can be manually entered or assayed using known analytical, chromatographic or spectroscopic techniques such as HPLC, HPAE PAD, TLC or gas chromatography. Information regarding concentration of the C5 and C6 sugar concentration and their composition is inputted into the dilution control unit either manually by the user or electronically.

The dilution control unit can adjust the dilution of the hemicellulose sugars in the dilution tank to a set concentration. A range of concentrations can be selected because in some cases, a sugar concentration too high can lead to undesired side products in the conversion reaction to form furfural, and a sugar concentration too low can lead to a lower amount of furfural product produced for a given system size. For example, the dilution control unit can adjust the dilution of the hemicellulose sugars to 2-10% or 4-8% relative to the aqueous sugar stream (wt/wt). In some cases, the dilution control unit can adjust the dilution of the hemicellulose sugars to at least 10, 9, 8, 7, 6, 5, 4, 3, 2 or 1% relative to the aqueous sugar stream (wt/wt). Alternative or in combination, the dilution control unit can adjust the dilution of the hemicellulose sugars to up to 1, 2, 3, 4, 5, 6, 7, 8, 9, or 10% relative to the aqueous sugar stream (wt/wt). In some cases, the dilution control unit adjusts the dilution of the hemicellulose sugars in the dilution tank to about 6% (wt/wt). The furfural-depleted aqueous stream can comprise water, acid and salt. In some cases, an anion of the salt is a conjugate base of the acid.

Dilution tank 111 comprises an output port for exiting of an aqueous sugar stream 202. Aqueous sugar stream 202 preferably has one or more of the following characteristics: total hemicellulose sugar concentration in the range of 2-20% wt/wt, with a total acid concentration of 0.1-2% wt/wt, and a total concentration of salt in the range of 2.5-7.5%. Dilution tank 111 is fluidly connected to reactor 113 such that the aqueous sugar stream 202 exiting the dilution tank 111 is directed to reactor 113.

Reactor 113 is also downstream and fluidly connect to a solvent feed tank 141 and heat exchanger 142. Solvent feed tank 141 is configured to hold an organic solvent (e.g., an S5 solvent as described in more detail below). Solvent feed tank 141 is upstream of and fluidly coupled to heat exchanger 142. Heat exchanger 142 is configured to heat an organic stream 204 from the solvent feed tank to at least 150, 160, 170, 180, 190, 200, 210, 220, 225, 230, 235 or 240° C. The heat exchanger 142 can also act as a reactor or can be fluidly coupled to a reactor downstream of it.

Thus, an organic stream 204 comprising an organic solvent (e.g., S5 solvent) is fed from tank 141 through a heat exchanger 142, where it is pre-heated. Preheating of organic stream 204 prior to combining with aqueous stream 202 can decrease the amount of time needed to heat biphasic reaction mixture 206 in reactor 113 and can provide increased yields or selectivity. Thus, the disclosure herein contemplates a system with a heating module upstream of a reaction vessel, wherein the heating module is configured for pre-heating an organic solvent prior to contacting of the organic solvent with hemicellulose sugars and reacting the two in the reactor.

The system described herein comprises a reactor configured to maintain a preheated solvent and an aqueous solution comprising hemicellulose sugars at a set temperature and pressure thereby converting C5 sugars, (e.g., xylose or arabinose) from the hemicellulose sugars into furfural. The reactor can be reactor 113 in FIG. 2. The dilution tank 111 is coupled directly or indirectly to reactor 113 such that the aqueous sugar stream 202 can flow from the dilution tank 111 to the reactor 113. The aqueous sugar stream 202 and organic stream 204 (after optional preheating at heat exchange 142) mix and optionally flow through the reactor 113. When reactor 113 is a batch reactor, the reactor is charged with an organic stream 204 and an aqueous stream 202, and set to a predetermined temperature (e.g., at least 180° C.) for a predetermined reaction time (e.g., 30-600 seconds), with a predetermined pressure (e.g., at least 1 bar above saturated steam pressure at the reactor temperature). When reactor 113 is a continuous flow reactor, the organic stream 204 and an aqueous stream 202 are joined together to allow mixing either through mechanic turbulence or in the presence of baffle or joint to allow mixing of the phases. The mixed streams flow through the reactor set to a predetermined temperature (e.g., at least 180° C.) at a predetermined flow rate to allow for a predetermined residence time (e.g., 30-600 seconds), with a predetermined pressure set to at least 1 bar above saturated steam pressure at the reactor temperature.

The predetermined temperature and reaction time in reactor 113 are controlled by a reaction control unit. The reaction control unit is operably connected to the heat exchanger and/or the reactor controls the temperature and/or pressure. The heat exchanger or reactor can be configured for heating contents to greater than 100, 120, 130, 140, 150, 160, 170, 180° C. The heat exchanger can be HX 114 in FIG. 2.

The reaction control unit can include a computer configured to receive input on the following parameters the identity, quantity, and concentration of acid, salt, and sugars of aqueous sugar stream 202 and using such variable to calculate the following: the amount of heat to provide the reactor, amount power to provide a heating unit coupled to the reactor, time to keep the contents in the reactor, speed of flow through a flow reactor. Such a computer is a specific computer that is also programmed to control the following processes in the system: input and output valves of reactor 113, pump controlling rate of the reactants through a flow reactor, or a combination thereof. In some instances, a reaction control unit can be pre-set at specific parameters for a given set of reaction conditions (e.g., temperature, reaction residence time, flow rate). Sugar composition of the hemicellulose sugars fed into the reactor tank can be assayed using known techniques. Information regarding concentration of the C5 and C6 sugar concentration and their composition is entered as input into the reaction control unit either manually by the user or electronically.

Upon sufficient conversion, the contents of reactor 113, biphasic reaction mixture 206, are can be cooled via heat exchanger 119. Alternatively or in combination, the contents can be allowed to cool through passive heat transfer or progressed through the system without a cooling step.

A filter such as filter 120 can be downstream and fluidically coupled to reactor 113 to filter solid particles from biphasic reaction mixture 206 to produce filtered reaction mixture 207. Filter 120 can have a mesh size configured to remove humins and solid particles. Filter 120 is operably coupled to phase separation 144. In cases lacking heat exchanger 119A and filter 120, reactor 113 is coupled to a phase separation 144 a device suitable for separating an organic phase from an aqueous phase (e.g., a centrifuge, a hydrocylon, a stator). The filtered reaction mixture 207 is moved to a separation module, which can include, for example, one or more distillation columns, centrifuges, filters, chromatographic columns, or condensors. The separation module in FIG. 2 comprises two phase separation units in series (144, 175) and a separator unit (145) downstream of the first phase separation unit (144) and the second separation unit (175).

The biphasic reaction mixture 206 or filtered reaction mixture 207 is separated by the separation module according to the following protocol. First, the biphasic reaction mixture 206 (or filtered reaction mixture 207) is separated by a first phase separation unit 144, e.g., a centrifuge, a hydrocylon, a stator or any other device suitable for separating the organic phase from the aqueous phase. Phase separation 144 separates biphasic reaction mixture 206 into a furfural-enriched organic stream 208 and an intermediate aqueous stream 210.

The furfural-enriched organic stream is diverted to a separator unit 145 (e.g., one or more distillation columns) to isolate furfural. Separation unit 145 is a device capable of separating furfural from furfural-enriched organic stream 208. Separation unit 145 separates furfural-enriched organic stream 208 to an isolated furfural product stream 230 and furfural-depleted organic stream 212. The isolated furfural stream 230 can be have furfural with a purity of greater than 90 or 95% pure. The furfural depleted organic stream includes one or more of the following signature elements: water in an amount up to 5% by weight; S5 solvent in amount up to 1% by weight; and at least two impurities, wherein the total amount of all impurities together is up to 5000 ppm by weight relative to furfural; wherein the impurities are selected from the group consisting of formic acid, levulinic acid, acetic acid, 5-chloromethylfuran-2-carbaldehyde, 5,5'-diformyl-2,2'-difuran, HMF, and HCl Separation unit 145 is fluidically coupled to the solvent feed tank 141 such that the furfural-depleted organic stream 212 can be directed to and recycled back into the system (e.g., to solvent feed tank 141) to minimize the amount of organic solvent required.

To ensure sufficient purity for recycling, two washes can be performed to at least a portion of furfural-depleted organic stream 212 using a first extractor 180 and a second extractor 170. The extraction modules are configured for extracting hydrophilic impurities from an organic phase solvent by contacting in a counter current mode with an aqueous phase comprising acid and salt. Each of extractors 180 and 170 are configured to treat at least a portion of the furfural-depleted organic stream 212 and are downstream of separation unit 145 and upstream of solvent feed tank 141. The first extractor 180 is coupled to a water reservoir and has a water inlet port. The first extractor 180 also includes two or more exit ports. A first exit port returns extracted-return organic stream 218 to the furfural-depleted organic stream 212. A second exit port removes aqueous waste stream 216 from the extractor. Thus, a stream of water 214 can be used to extract a portion of the furfural-depleted organic stream 212 with extractor 180. The extractor can be a centrifuge or any known biphasic extraction apparatus. The extracted-return organic stream 218 is rerouted to join furfural-depleted organic stream 212.

The system can also include a second extractor 170 for conducting a second wash. Extractor 170 is coupled to a basic aqueous solution reservoir comprising an aqueous basic solution (e.g., pH>10). The second extractor 170 is configured to effectively remove organic acids such as levulinic, formic and acetic acids, as well as residual humins, HMF, and other reaction byproducts from furfural-depleted organic stream 212. Flowing basic aqueous solution 224 from the basic aqueous solution reservoir is used to remove residual acid from the furfural-depleted organic stream 212 in the extractor 170. At least a portion of the furfural-depleted organic stream 212 is directed to extractor (e.g., phase separator) 170 along with the basic aqueous solution 224. The two phases are mixed and separated in the extractor 170. A first outlet of extractor 170 removes basic aqueous waste stream 226 to a waste management system. A second outlet of extractor 170 returns purified-return organic stream back to the furfural-depleted organic stream 212.

The purified return organic stream 228 is coupled to rejoin the furfural-depleted organic stream 212. The furfural-depleted organic stream 212 is coupled to solvent feed tank 141 to complete the organic solvent recycling loop.

The overall loop structure of the organic solvent (e.g., solvent feed tank 141 to reactor 113, to separation module 144/145/175, back to the solvent feed tank 141) allows the system to run with minimal use of organic solvent and minimal organic waste. Over the course of one or more loops, a portion of the organic solvent can be removed from the system as organic waste at an outlet such as 240 designated for organic waste purge stream that is upstream of solvent feed tank 141 but downstream of the separation module.

As described above, separation module can include two phase separation units in series (144, 175) and a distillation unit (145) downstream of both the first phase separation unit (144) and the second separation unit (175). Intermediate aqueous stream 210 which exits from the first phase separation unit 144 comprises residual furfural from biphasic reaction mixture 206 due to an imperfect partition coefficient of furfural between the aqueous and organic layers. To recover at least a portion of this residual furfural, intermediate aqueous streams 210 and at least a portion of furfural-depleted organic stream 212 are mixed at a second phase separation unit 175, and separated to form an intermediate organic stream 220 and a furfural-depleted aqueous stream 222. Preferably, the portion of the furfural-depleted organic stream 212 that is removed to the second phase separation unit 175 occurs after the first water 214 wash by extractor 180 and before the second base 224 wash by extractor 170. The mixing and separation at phase separation unit 175 can form a counter current extraction process, a turbulent mixing and separation, or a batch wise extraction separation process. Intermediate organic stream 220 is directed via a conduit from the second phase separation unit 175 to the first phase separation unit 145, thereby forming an organic enriched loop (e.g., 145/175/145/175 counter stream) and increasing the conversion percentage of xylose and selectivity of the conversion to furfural which is subsequently isolated. In addition to stream 220, a furfural depleted aqueous stream 222 exits phase separation unit 175. This aqueous stream is directed with a conduit back to dilution tank 111 to complete the cycle of the aqueous solutions in the system (e.g., 111/113/144/175/111).

The system can be configured to recycle aqueous streams. The system can be configured to recycle at least 70, 75, 80, 85, 90, or 95% of the furfural-depleted aqueous solution. The furfural depleted aqueous solution can be a stream coupled to 175 and 111 in FIG. 2. By recycling the aqueous solution, the system is able to generate a low amount of aqueous waste. At least a portion of aqueous recycle stream can be diverted to purge stream 176 to waste. Purge stream 176 allows control over the recycle level of the aqueous recycle stream, providing an outlet for water soluble byproducts and/or unreacted $C_6$ sugars.

Individual components of the system are described in greater detail. Each of these components and details thereof can be applied similarly to the general overview of the system described in FIG. 2.

The dilution control unit can adjust the dilution of the hemicellulose sugars in the dilution tank to a set concentration. A range of concentrations can be selected because in some cases, a sugar concentration too high can lead to undesired side products in the conversion reaction to form furfural, and a sugar concentration too low can lead to a lower amount of furfural product produced for a given system size. For example, the dilution control unit can adjust the dilution of the hemicellulose sugars to 2-10% or 4-8% relative to the aqueous sugar stream (wt/wt). In some cases, the dilution control unit can adjust the dilution of the hemicellulose sugars to at least 10, 9, 8, 7, 6, 5, 4, 3, 2 or 1% relative to the aqueous sugar stream (wt/wt). Alternative or in combination, the dilution control unit can adjust the dilution of the hemicellulose sugars to up to 1, 2, 3, 4, 5, 6, 7, 8, 9, or 10% relative to the aqueous sugar stream (wt/wt).

In some cases, the dilution control unit adjusts the dilution of the hemicellulose sugars in the dilution tank to about 6% (wt/wt). The system described herein can comprise a dilution tank operably connected to the dilution control unit and a furfural-depleted aqueous stream from a separation module of the system. The furfural-depleted aqueous stream can comprise water, acid and salt. In some cases, an anion of the salt is a conjugate base of the acid.

The system described herein can further comprise a reaction control unit. A reaction control unit can be configured to adjust temperature, acid concentration, or salt concentration in reactor 113 based on chemical composition of the hemicellulose sugars.

The system can comprise a reaction control unit configured to adjust the acid concentration in reactor 113 based on chemical composition of the hemicellulose sugars. For example, the system can comprise a reaction control unit configured to increase acid concentration when the hemicellulose sugars comprise one or more C6 sugars relative to the acid concentration when the hemicellulose sugars do not comprise one or more C6 sugars. In some cases, the reaction control unit can set the acid concentration to at least 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.5, 3.0, 3.5, 4.0, 4.5, 5.0, 6.0, 7.0, 8.0, 9.0 or 10.0% relative to the weight of the aqueous sugar stream (wt/wt).

In one example, when the hemicellulose sugars are substantially pure xylose, the reaction control unit is set to maintain or reach acid amount in the dilution tank between 0.1 and 1.0% relative to the aqueous sugar stream (wt/wt). In some cases wherein the hemicellulose sugars comprise at least 2% C6 sugars relative to C5 sugars (wt/wt), the reaction control unit is set to maintain or reach an acid amount of at least 1.2% relative to the aqueous sugar stream (wt/wt). If the acid concentration in the dilution tank is lower than the set level, then the reaction control unit operates, e.g., an input valve or flow modulator to cause an increase in acid flow from an acid stream or reservoir into the dilution tank 111. If the acid concentration in the dilution tank 111 is higher than the set level, then the control unit controls operates, e.g., an input valve or flow modulator to cause an increase of aqueous sugar stream into dilution tank 111. The reactor can be reactor 113 of FIG. 2.

In addition to acid concentration, the reaction control unit can be configured to adjust the salt concentration in the reactor 113 based on chemical composition of the hemicellulose sugars. The reaction control unit can adjust the salt concentration in the dilution tank to at least 0.3, 0.4, 0.5, 0.6, 0.7, 0.8, 0.9, 1.0, 2.0, 3.0, 4.0, 5.0, 6.0, 7.0, 8.0% relative to the aqueous sugar stream (wt/wt). The reaction control unit can add additional salt to increase the salt concentration or can add additional aqueous solution or water to lower the salt concentration.

The reaction control unit configured to adjust temperature of the reactants in reactor 113, reaction residence time for reactor 113, or a combination thereof when the hemicellulose sugars comprise one or more C6 sugars. The system can comprise a reaction control unit configured to adjust temperature when the hemicellulose sugars comprise one or more C6 sugars. For example, the reaction control unit is configured to increase the temperature by activating a heating unit or decrease the temperature by either deactivating a heating unit or activating a cooling unit. In some cases, the reaction control unit is configured to increase the reaction temperature to at least 100, 110, 120, 130, 140, 150, 160, 170, 180, 190, 200, 210, or 220° C. In cases wherein the hemicellulose sugars comprise at least 5% C6 sugars, the reaction control unit can be configured to increase the temperature to at least 170, 180, 190, or 200° C. The system can comprise a reaction control unit configured to adjust reaction residence time when the hemicellulose sugars comprise one or more C6 sugars. In some cases, the reaction control unit is configured to increase the reaction residence time to at least 100, 400, 800, 1200, 1600, 2000, 2400 seconds. In some cases, the reaction control unit is configured to set the reaction residence time to less than 2400, 2200, 2000, 1800, 1600, 1400, 1200, 1000, 800, 400, 200, 100 seconds. The reaction control unit can be coupled to reactor 113 of FIG. 2. For example, the reaction control unit can be configured to adjust temperature, reaction residence time, or a combination thereof, of reactor 113 when the reactor comprises hemicellulose sugars, wherein the hemicellulose sugars comprise one or more C6 sugars.

Thus, in one embodiment, a system herein comprises a solvent feed tank, a dilution feed tank, a reactor downstream of the solvent feed tank and the dilution feed tank, and a separation module downstream of the reactor; wherein the separation module is configured for separating furfural, an aqueous stream, and an organic solvent stream; wherein (i) the solvent feed tank is configured to preheat solvent separated by and exiting from the separation module; (ii) the dilution feed tank is configured to dilute the hemicellulose sugars with the aqueous stream separated by and exiting from the separation module; and (iii) the reactor is configured to maintain the preheated solvent and the diluted hemicellulose sugars at a set temperature and pressure thereby converting xylose and/or arabinose from the hemicellulose sugars into furfural.

The system described herein can comprise a separation module for separating a reaction mixture into a furfural-enriched product stream, an aqueous stream and an organic solvent stream, wherein (i) the furfural-enriched product stream has a furfural purity of at least 90%; (ii) the aqueous stream comprises acid and less than 1% (wt/wt) organic solvent and less than 2% (wt/wt) hemicellulose sugars; and (iii) the organic solvent stream comprises an S5 solvent and less than 1% (wt/wt) non-S5 solvent impurities.

The separation module can comprise one or more distillation columns. In some cases, the system comprises a separation module comprising two distillation columns. The separation module can comprises one, two, three, four, or more extractors. An extractor can be any apparatus capable of carrying out an extraction, for example an aqueous organic extraction. In some cases, an extractor is a centrifuge or an extraction column.

One or more of the processes described herein is depicted by FIG. 2. For example, the biphasic reaction mixture comprising furfural is the stream exiting reactor 113 of FIG. 2. The reaction mixture can be optionally cooled in heat exchanger 119A, optionally filtered in filter 120, or a combination thereof. Optionally, heat exchanger 119A is coupled with another heat exchanger in the system, so energy removed from the solution in 119A is utilized to heat another part of the cycle thus reducing the overall energy requirements of the process. The reaction mixture can be separated by phase separation 144 to a furfural-enriched organic stream which can be directed to 145, and an intermediate aqueous stream which can be directed to phase separation 175. At least a portion of the furfural from the furfural-enriched organic stream can be removed by 145 (for example, by distallation). The furfural that is removed can be directed as isolated furfural stream 1440-P1. The resulting furfural-depleted organic stream can be directed from 145 toward optional wash 180. The intermediate aqueous stream can be contacted with at least a portion of the furfural-depleted organic stream at 175 to produce a biphasic extraction mixture. The biphasic extraction mixture can be separated as two streams exiting 175. The intermediate organic stream can be a stream exiting 175 and can be reintroduced into the furfural-enriched organic stream, for example at or before 145. The furfural-depleted aqueous stream can be a stream from 175. The furfural-depleted aqueous stream can be utilized to dilute feedstock hemicellulose sugars to generate additional biphasic reaction mixture. In such cases, the furfural-depleted aqueous stream can be coupled to dilution tank 111. In some cases, at least a portion of the furfural-depleted organic stream is utilized to dilute feedstock hemicellulose sugars to generate additional biphasic reaction mixture. In such cases, at least a portion of the furfural-depleted organic stream can be coupled to dilution tank 141.

In some cases, at least a portion of the furfural-depleted aqueous stream is purged from the system. In such cases, at least a portion of the furfural-depleted aqueous stream is removed between 175 and 111. In some cases, at least a portion of the furfural-depleted organic stream is purified by base or water extraction. In such cases, the furfural-depleted organic stream can be purified by base extraction at 170 or water extraction at 180. The processes described herein can comprise one or more organic streams that comprise an S5 solvent. The processes described herein can comprise a continuous loop. In some cases, at least 60%, 70%, 80%, or 90% of furfural in the first biphasic solution becomes isolated furfural.

Provided herein is a process comprising: (a) separating a biphasic reaction mixture comprising furfural to form a furfural-enriched organic stream and an intermediate aqueous stream; (b) removing at least a portion of the furfural from the furfural-enriched organic stream to produce an isolated furfural stream and a furfural-depleted organic stream; (c) contacting the intermediate aqueous stream with at least a portion of the furfural-depleted organic stream to produce a biphasic extraction mixture; (d) separating from the biphasic extraction mixture a furfural-depleted aqueous stream and an intermediate organic stream; and (e) reintroducing the intermediate organic stream into the furfural-enriched organic stream.

In some cases, at least a portion of the furfural-depleted organic stream is utilized to dilute feedstock hemicellulose sugars to generate additional biphasic reaction mixture. In some cases, at least a portion of the furfural-depleted aqueous stream is utilized to dilute feedstock hemicellulose sugars to generate additional biphasic reaction mixture. At least a portion of the furfural-depleted aqueous stream can be purged from the system. At least a portion of the furfural-depleted organic stream is purified by base or water extraction.

The organic streams described by the processes herein can comprise an S5 solvent. A sufficient quantity of S5 solvent can be recycled so the only loss of S5 solvent from the system is the amount of solvent S5 that partitions into the aqueous phase through the extraction processes described herein. An S5 solvent can be selected to have a very low solubility in water to allow less than 0.5% S5 solvent loss from the system compared to amount of the furfural produced daily, wt/wt.

The processes described herein can comprise a continuous loop.

Further provided herein is a process to produce furfural, comprising: (a) feeding a reactor with an aqueous sugar stream and an organic stream to form a biphasic reaction mixture; wherein the aqueous sugar stream comprises xylose, salt, and an acid; wherein the acid is at normality of 0.05 to 2; (b) heating the biphasic reaction mixture to convert at least a portion of the xylose to furfural; (c) separating the biphasic reaction mixture to produce a furfural-depleted organic stream, an isolated furfural stream, and a furfural-depleted aqueous stream; and (d) recycling at least a portion of the furfural-depleted organic stream to the feed of the reactor. The process can further comprise (e) washing the furfural-depleted organic stream with water and separating the phases to form an aqueous waste stream and an extracted-return organic stream. The processes described herein can further comprise: (f) contacting a portion of the furfural-depleted organic stream with a basic aqueous stream of pH>10.0 to form a basic extraction mixture; and (g) separating the basic extraction mixture to obtain a purified-return organic stream and a basic aqueous waste stream comprising impurities.

The acid can be at a normality of up to 0.05, 0.1, 0.2, 0.3, 0.4, 0.5, 0.6, 0.7, 0.8, 0.9, 1.0, 1.2, 1.4, 1.6, 1.8, 2.0, 3.0, 4.0, or 5.0. In some cases, the acid is at a normality of about 0.05 to 2.0 inclusive. In some cases, the acid is at a normality less than 2, 1.8, 1.6, 1.4, 1.2, 1.0, 0.8, 0.6, 0.4, 0.2 or 0.1. The acid identity and normality can be selected as described herein.

One or more of the processes to produce furfural described herein can be depicted by FIG. 2. For example, the reactor can be reactor 113. The aqueous sugar stream can be the stream coupled directly or indirectly to dilution tank 111 and reactor 113. The organic stream can be the stream coupled directly or indirectly to solvent feed tank 141 and reactor 113. The biphasic reaction mixture can be heated in reactor 113 to convert at least a portion of the xylose to furfural. The biphasic reaction mixture can be separated by a one or more components of a separation module as described herein. For example, the biphasic reaction mixture can be separated by 144, 145, and 175 of FIG. 2. The biphasic reaction mixture is separated to produce a furfural-depleted organic stream, an isolated furfural stream, and a furfural-depleted aqueous stream. The furfural-depleted organic stream can be a stream exiting 145. The isolated furfural stream can be stream 1440-P1. The furfural-depleted aqueous stream can be a stream exiting 175 and coupled directly or indirectly to dilution tank 111. The process can further comprise washing the furfural-depleted organic stream with water and separating the phases to form an aqueous waste stream and an extracted-return organic stream. The washing and separating can occur at 180. The aqueous waste stream can exit the system from 180. The extracted-return organic stream can be coupled directly or indirectly to solvent feed tank 141. The extracted-return organic stream or the furfural depleted organic stream can be contacted with a basic aqueous stream of pH>10 at to form a basic extraction mixture at 170. The basic extraction mixture at 170 can be separated to obtain a purified-return organic stream which is coupled directly or indirectly to solvent feed tank 141; and a basic aqueous waste stream comprising impurities which exits the system at 170.

Further provided herein is a process to produce furfural comprising: preheating an organic solvent to form a preheated organic stream; contacting the preheated organic stream with an aqueous sugar stream comprising xylose, an acid, and a salt to form a biphasic reaction mixture; heating the biphasic reaction mixture at a predetermined temperature for a predetermined time to convert at least a portion of the xylose to furfural.

The predetermined temperature or time can be calculated based on the composition of the aqueous sugar stream. For example, the predetermined temperature can be at least 170° C. The predetermined time can be 60 to 1800 seconds. The organic solvent can be an S5 solvent, for example, tetralin. The reactor can be a continuously mixed reactor. The pressure of the reaction can be at least 1 bar pressure higher than the equivalent saturated steam pressure of the reaction. In some cases, at least 80% of the xylose or xylose equivalent is converted to furfural (molar yield). The process can further comprise isolating the furfural. In some cases, the acid is HCl. In cases, wherein the acid is HCl, the salt can comprise chloride.

As used herein, "about" refers to +/−10, 9, 8, 7, 6, 5, 4, 3, 2 or 1% when in reference to a quantitative amount.

As used herein, "S5 solvent" refers to a solvent that is substantially immiscible with water and has an affinity for furfural greater than the affinity of water for furfural. An S5 solvent can be further characterized as having a boiling point sufficiently higher than the boiling point of furfural to allow separation/purification of the furfural by distillation.

An S5 solvent is selected from the group consisting of optionally substituted alkane, alkene, alkyne, and aromatic. In some embodiments, S5 solvent is a compound selected from the group consisting of optionally substituted alkane, alkene, alkyne, and aromatic; wherein the compound is optionally substituted with one or more halogens, alcohols, or esters. In some embodiments, S5 solvent is a compound selected from the group consisting of optionally substituted alkane, alkene, alkyne, and aromatic; wherein the compound is optionally substituted with one or more functional groups; wherein each functional group consists of one or more atoms independently selected from the group consisting of C, H, N, O, S, F, Cl, Br, and I.

An S5 solvent can be an optionally substituted aromatic. For example, S5 solvent can be selected from the group consisting of benzene, toluene, ethylbenzene, diethylbenzene, dipropylbenzene, dimethylethylbenzene, 2-ethyl-2,4-dimethylbenzene, butylbenzene and tetralin. In some embodiments, S5 solvent is a halogenated aromatic. Non-limiting examples of S5 solvent can include chlorobenzene, bromobenzene, iodobenzene, dichlorobenzene, dibromobenzene, bromochlorobenzene, trichlorobenzene, and chlorinateddiphenyl.

An S5 solvent can be an optionally substituted alkane or an alkane derivative. For example, a substituted alkane can be an alkanol, alkanone, or alkanoic acid, or alkanoic ester. Some non-limiting examples of S5 solvent can be isophorone, octylalcohol, (for example, 1-octanol, 2-octanol, 3-octanol, or 4-octanol), octylacetate, octanone, octanoic acidethylacetate, or any combination thereof. In some embodiments, an optionally substituted alkane is a halogenated alkane. A halogenated alkane can be dichlormethane, bromomethane, iodomethane, bromochloromethane, chloroform, bromoform, chloroethane, bromoethane, 1,1-dichloroethane, 1,2-dichloroethane, or 1,1,1-trichloroethane, for example.

An S5 solvent can be selected from a group consisting of, aromatics, halogenated aromatics, chlorinated diphenyls, halogenated alkanes, and alkane derivatives; wherein the S5 solvent has a boiling point higher than the boiling point of furfural. An S5 solvent can be selected from a group consisting of higher boiling point aromatics, (for example, diethylbenzene, dipropylbenzene, dimethylethylbenzene, 2-ethyl-2,4-dimethylbenzene, butylbenzene, and tetralin), higher boiling point heteroatom aromatics (for example quinoline, isoquinoline, and indole), halogenated aromatics, (for example, dichlorobenzene, dibromobenzene, bromochlorobenzene and trichlorobenzene), chlorinated diphenyls, halogenated alkanes (for example, 1,1,1-trichloroethane and chloroform), and alkane derivatives (for example, octylalcohol and octylacetate) (see, e.g., U.S. Pat. No. 4,533,743, the content of which is incorporated herein by reference).

An S5 solvent can be a liquid aromatic hydrocarbon. A "liquid aromatic phase" as used herein is understood to mean a liquid phase comprising at least one aromatic hydrocarbon compound. In the process described herein, the liquid aromatic phase can comprise one or more aromatic hydrocarbon compounds. As used herein, an aromatic hydrocarbon compound is understood to be a compound that comprises a benzene or naphthalene ring, which ring is optionally substituted by one or more alkyl groups. The term "alkyl" includes both straight chain and branched chain alkyl groups. If substituted, the benzene or naphthalene ring is preferably substituted with one to four, more preferably one or two alkyl groups. Preferably the alkyl group contains 1 to 6, more preferably 2 to 4 carbon atoms. Preferably the liquid aromatic phase includes a C1-C6 alkyl substituted benzene or a C1-C6 alkyl substituted naphthalene or a mixture thereof.

The one or more aromatic hydrocarbon compounds are suitably capable to act as a solvent in which furfural is soluble (at an extraction temperature and pressure) and are preferably substantially water-immiscible. A substantially water-immiscible aromatic hydrocarbon compound refers to an aromatic hydrocarbon compound having a solubility in water of less than 500 mg/kg, at ambient temperature (20° C.) and pressure (1 bar absolute).

An S5 solvent can be selected from naphthalene, tetralin, quinoline, or a combination thereof. In some cases, an S5 solvent comprises at least 40, 50, 60, 70, 80, 90, 95, 96, 97, 98, 99, or 99.5% tetralin wt/wt.

An S5 solvent can comprise naphthalene. Naphthalene has a boiling point (218° C.) which is higher than that of furfural, is water-immiscible and has high affinity to furfural, indicating that it should be well suited to extracting furfural from an aqueous phase comprising furfural having the advantage that furfural can be distilled or evaporated out of naphthalene and minimal energy (see, e.g., WO2011161141, the content of which is incorporated herein by reference). Furfural is distilled 1440 to obtain the furfural product 1440-P1 and to recover S5 solvent for recycling. The conversion of xylose to furfural is greater than 90%, 92%, 94%, 96%, 98%, 99%, the molar yield is greater than 80%, 85%, 90%, or 95%, with selectivity greater than 80%, 85%, 87%, 89%, 90%, 93%, 95%, or 97%. It is preferred to distill the furfural versus the solvent for energy conservation and product purity An S5 solvent can comprise tetralin. 1,2,3,4-tetrahydronaphthalene (tetralin) has a boiling point of 206-208° C., which is much higher than the boiling point of furfural, and a melting point of −35.8° C. and is therefore always liquid at practical range of operation. It is water-immiscible and has high affinity to furfural, indicating that it should be well suited to extracting furfural from an aqueous phase comprising furfural having the advantage that furfural can be distilled or evaporated out of tetralin and minimal energy. Furfural is distilled 1440 to obtain the furfural product 1440-P1 and to recover S5 solvent for recycling. The conversion of xylose to furfural is greater than 90%, 92%, 94%, 96%, 98%, 99%, the molar yield is greater than 80%, 85% 90% 95%, with selectivity greater than 80%, 85%, 87%, 89%, 90%, 93%, 95%. 97%. It is preferred to distill the furfural versus the solvent for energy conservation and product purity.

An S5 solvent can comprise quinoline. Quinoline has a boiling point of 237° C., which is much higher than the boiling point of furfural, and a melting point of −35.8° C. and is therefore always liquid at practical range of operation. It is water-immiscible and has high affinity to furfural, indicating that it should be well suited to extracting furfural from an aqueous phase comprising furfural having the advantage that furfural can be distilled or evaporated out of quinoline and minimal energy. Furfural is distilled 1440 to obtain the furfural product 1440-P1 and to recover S5 solvent for recycling. The conversion of xylose to furfural is greater than 90%, 92%, 94%, 96%, 98%, 99%, the molar yield is greater than 80%, 85% 90% 95%, with selectivity greater than 80%, 85%, 87%, 89%, 90%, 93%, 95%. 97%. It is preferred to distill the furfural versus the solvent for energy conservation and product purity.

"Hemicellulose sugars" as described herein refers to any one or more naturally occurring or synthetically-derived monomeric, dimeric, or oligomeric sugar that can be found in hemicellulose or derived from hemicellulose. Hemicellulose sugars can be a hydrolysate stream from a biomass hydrolysis. A hydrolysate stream refers to a stream directly from hydrolysis, or in some cases, at least a portion of the stream can be a purified. Alternatively or in combination, hemicellulose sugars can be purified monomeric sugars that are derived from hemicellulose.

Preferably a hemicellulose sugar or hemicellulose sugar stream comprises xylose. For example, a hemicellulose sugars described herein can comprise at least 40, 50, 60, 70, 80, 90, 95, 96, 97, 98, 99 or 99.9% xylose (wt/wt). In some cases, the hemicellulose sugar is substantially pure xylose. For example, a hemicellulose sugars can comprise at least 90, 95, 99 or 99.9% xylose (wt/wt).

The hemicellulose sugars can further comprise one or more other C5 sugars. For example, in some instances, the hemicellulose sugars can comprise arabinose. In some cases, hemicellulose sugars arabinose at a concentration of up to 1, 2, 3, 4, 5, 6, 7, 8, 9, 10, 15, 20, 25, 30, 35, 40, 45, 50, or 60% arabinose relative to total sugars (wt/wt). In some cases, the hemicellulose sugars comprise one or more C5 sugars selected from the group consisting of arabinose, lyxose, ribose, xylose, ribulose, and xylulose.

The hemicellulose sugars can comprise one or more C6 sugars in addition to the xylose. For example, the hemicellulose sugars can comprise at least 1, 2, 3, 4, 5, 6 or 7 different C6 sugars. Some non-limiting examples of C6 sugars are allose, altrose, glucose, mannose, gulose, idose, galactose, talose, psicose, fructose, sorbose or tagatose. In some cases, each C6 sugar can be selected from the group consisting of glucose, mannose, and galactose. For example, in one instance a hemicellulose sugar mixture herein comprises xylose and glucose. When the hemicellulose sugars comprise C6 sugar(s) they can comprise at least 0.1, 0.5, 1.0, 2.0, 3.0, 4.0, 5.0, 6.0, 7.0, 8.0, 9.0, 10.0, 12.0, 14.0, 16.0, 18.0, or 20.0% C6 sugars wt/total weight of sugars. In some cases, the hemicellulose sugars can comprise only trace amounts of C6 sugars, for example, the total amount of C6 sugars relative to total sugars (wt/wt) can be up to 0.1, 0.5, 1.0, 2.0, or 3.0%.

The hemicellulose sugars used to produce furfural can be a refined sugar mixture stream. For example, the hemicellulose sugars can be a sugar mixture stream produced from refining. The sugar mixture can be a refined mix sugar stream comprising ash at a concentration of up to 1%, 0.5%, 0.1%, 0.05%, or 0.01%, relative to dry sugars (wt/wt); wherein the ash comprises up to 500, 250, or 100 ppm metallic cations and less than 100, 50, 30, or 20 ppm sulfur relative to dry sugars. In some cases, a refined sugar mix stream is particularly suitable for conversion processes that require catalysts that are sensitive to ash elements or to sulfur compounds.

The hemicellulose sugars can further comprise less than 5000 ppm in total (wt relative to xylose wt) in said composition of elements; wherein said elements are Na, Ca, Cu, Fe, K, Mg, Mn, S and P.

The hemicellulose sugars can have a defined carbohydrate composition that is dependant of the biomass feedstock from which it was extracted. In cases wherein the hemicellulose sugars comprise a hydrolysate, such as a refined sugar mixture stream, the composition of the hemicellulose sugars can be dependent on the carbohydrate composition of the biomass feedstock from which it is extracted. For example, a refined sugar mixture stream derived from extraction of hardwood or sugar cane can comprise a relatively large fraction of C5 sugars because hardwood feedstock and sugar cane bagasse feedstocks comprise a large fraction C5 sugars, i.e., xylose and arabinose.

The hemicellulose sugars described herein can be extracted from a bagasse feedstockor a feedstock comprising bagasse. In one example, C5 sugar stream from baggase can comprise more than 80%, 81%, 82%, 83%, 84%, 85% C5 sugars (wt/wt DS). These C5 sugars can comprise more than 65%, 68%, 70%, 72%, 74%, 76% xylose (wt/wt DS). The remaining can include arabinose. Additionally, the remainder can include one or more of the following: glucose, mannose, fructose, galactose and disaccharides. For example, some hemicellulose sugars herein comprise about 5%, 6%, 7%, 8% 9%, 10%, 11%, 12% (wt/wt DS) glucose, about 0.5%, 1%, 1.5%, 2% (wt/wt DS) mannose, about 0.5%, 1%, 1.5% (wt/wt DS) fructose, about 0.3%, 0.5%, 1%, 1.5%, 2%, 2.5%, 3% (wt/wt DS) galactose, up to 8%, 7%, 6%, 5%, 4%, 3% (wt/wt DS) disaccharides. In one preferred embodiment, a sugar stream comprises about 69% (wt/wt DS) xylose and about 18% arabinose that the two most concentrated sugars are xylose and arabinose. The methods herein can be used to convert both the xylose and arabinose in the hemicellulose sugar stream to furfural in the same reaction.

The hemicellulose sugars can match sugar mixture 1836 in purity, wherein sugar mixture 1836 is a refined sugar stream. Such mixture can have a higher fraction of $C_5$ carbohydrates to C6. In one instance a sugarstream from bagasse can comprise more than 85% by weight xylose and more than 3% by weight arabinose out of total sugar. In another instance, comprises more than 88% by weight xylose and more than 4.5% by weight arabinose out of total sugars.

A hydrolysate sugar mixture from eucalyptus, can comprise more than 80%, 81%, 82%, 83%, 84%, 85%, 86%, 87%, or 88% by weight xylose to total sugar. The sugars in the hemicellulose sugar mixture can be predominantly sugar monomers. In some cases, it can be advantageous to use the sugar mix streams 1836 and/or 1837-A as the raw material for making furfural due to high purity and unique compositions of these streams.

The "aqueous sugar stream" described herein can be defined as an aqueous stream comprising hemicellulose sugars; wherein at least a portion of the hemicellulose sugars are to be converted to furfural. The aqueous sugar stream can comprise hemicellulose sugars diluted with water or another aqueous solution or aqueous stream described herein. The aqueous sugar stream can be a stream exiting a dilution tank. For example, the aqueous sugar stream can be the stream exiting dilution tank 111 in FIG. 2. The aqueous sugar stream can be a stream coupled to dilution tank 111 and coupled directly or indirectly to reactor 113 in FIG. 2. The aqueous sugar stream can be a stream comprising hemicellulose sugars; wherein at least a portion of the hemicellulose sugars are to be converted to furfural.

The aqueous sugar stream described herein can comprise hemicellulose sugars described herein. The aqueous sugar stream can comprise at least 1, 2, 3, 4, 5, 6, 7, 8, 9, 10, 11, 12, 13, 14, 16, 18, 20, 25, 30, 35, 40, 45, or 50% hemicellulose sugars wt/wt. Alternatively or in combination, the aqueous sugar stream can comprise less than 40, 35, 30, 25, 20, 20, 15, 14, 13, 12, 11, 10, 9, 8, 7, 6, 5, 4, 3, 2, or 1% hemicellulose sugars (wt/wt). For example, the aqueous sugar stream can comprise 1-12%, 2-10% or 4-8% hemicellulose sugars (wt/wt). In some cases, the aqueous sugar stream comprises about 6% hemicellulose sugars (wt/wt).

The aqueous sugar stream can comprise xylose. In some cases, the aqueous sugar stream comprises between about 70% and about 90% xylose (wt/wt, sugar dry solid basis).

The aqueous sugar stream can comprise between about 3% and about 15% arabinose (wt/wt, sugar dry solid basis).

The aqueous sugar stream can comprise at least 1% and up to 8% C6 sugar relative to xylose (wt/wt).

The aqueous sugar stream can further comprise less than 5000 ppm in total (wt relative to xylose wt) in said composition of elements; wherein said elements are Ca, Cu, Fe, K, Mg, Mn, S and P.

In some cases, the aqueous sugar stream comprises 5, 6, 7, 8 or 9 of the following characteristics: (i) a ratio of oligosaccharides to total dissolved sugars of not more than 0.10 weight/total sugar weight; (ii) a ratio of xylose to the total dissolved sugars of at least 0.50 weight/total sugar weight; (iii) a ratio of arabinose to total dissolved sugars of not more than 0.15 weight/total sugar weight; (iv) a ratio of galactose to total dissolved sugars of not more than 0.05 weight/total sugar weight; (v) a ratio of the sum of the glucose and fructose to total dissolved sugars of not more than 0.15 weight/weight; (vi) a ratio of mannose to total dissolved sugars of not more than 0.05 weight/weight; (vii) a ratio of fructose to total dissolved sugars of not more than 0.10 weight/weight; (viii) phenols in an amount of not more than 1000 ppm; (ix) hexanol in an amount of not more than 0.1% weight/weight: and (x) less than a total of 1000 ppm of the elements Ca, Cu, Fe, K, Mg, Mn, S and P relative to total sugar dry solid.

In some cases, the aqueous sugar stream comprises a ratio of oligosaccharides to total dissolved sugars is not more than 0.05 or 0.07. The aqueous sugar stream can comprise a ratio of xylose to total dissolved sugars can be at least 0.40 weight/weight. The aqueous sugar stream can comprise a ratio of xylose to total dissolved sugars can be at least 0.70 or 0.80 weight/weight. In some cases, the ratio of the sum of glucose and fructose to total dissolved sugars is not more than 0.09 or 0.05. In some cases, the aqueous sugar stream comprises phenols in an amount up to 60 ppm or 0.05 ppm.

Figure 3:
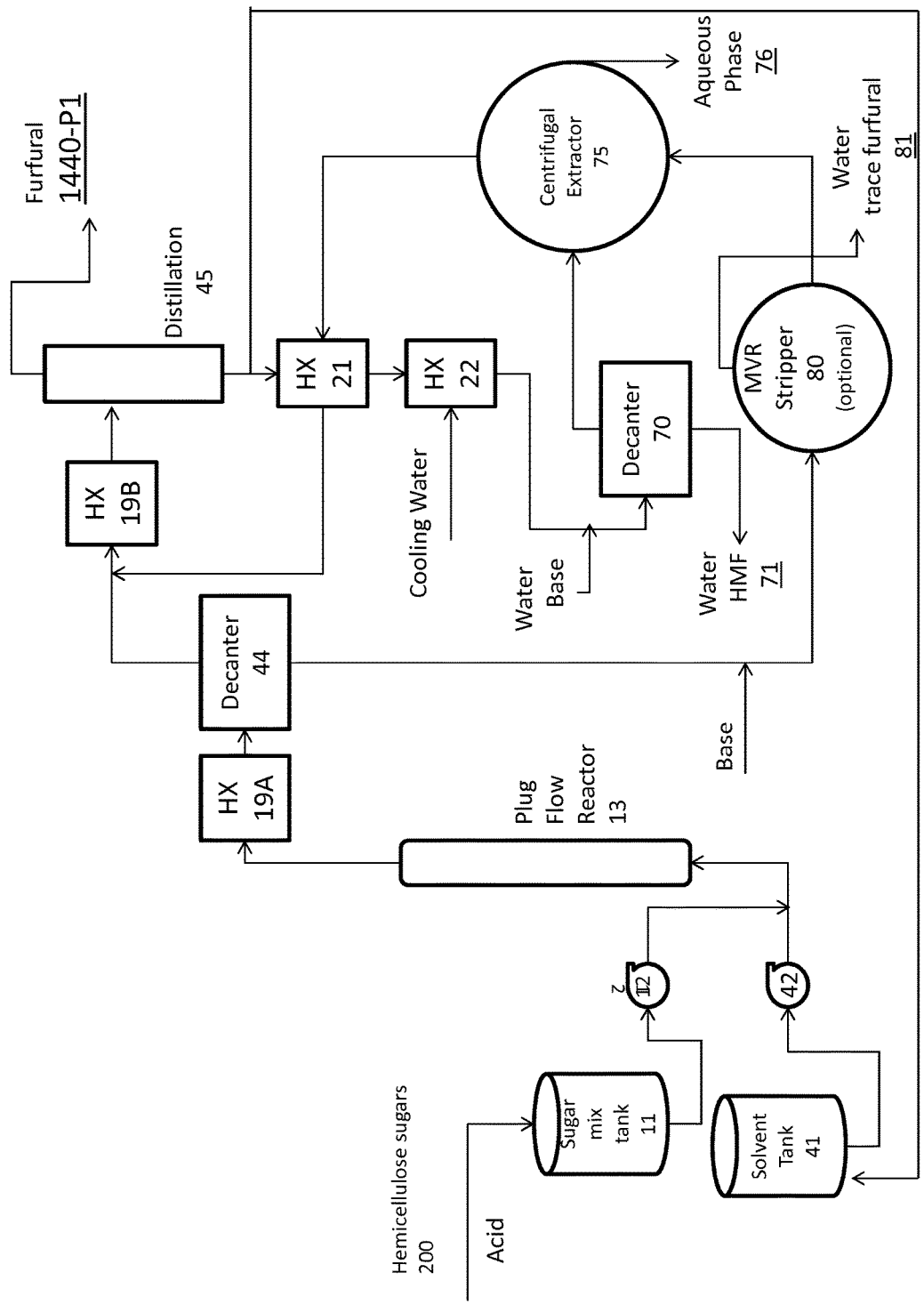
FIG. 3 shows a flow scheme for conversion of a hemicellulose sugar stream to a furfural stream.

An alternative embodiment of the disclosure is schematically described in FIG. 3. In general, hemicellulose sugars comprising a pentose (e.g., xylose and/or arabinose) (1837A or 1836), such as a hydrolysate stream (whether polished/purified or not) is mixed with a mineral acid catalyst (for example, $H_2SO_4$, HCl, etc.) in a sugar mixture tank 311. The mixed sugar/acid/salt solution preferably contains 1% to 10% by weight of an acid (e.g., HCl). The mixture in the sugar mixture tank 11 can be maintained at a temperature desired for sugar conversion to furfural. In some instances, the sugar mixture in sugar mixture tank 311 is maintained and fed at 60-65° C.

While the acid and hemicellulose are mixed in sugar mixture tank 311, solvent tank 341 is configured to maintain an S5 solvent. In some instances, solvent tank 341 is maintained at an elevated temperature (e.g. at least 100, 120, 140, 160, 170, or 180° C.). The solvent tank 341 is connected to plug flow reactor, which is situated downstream from the solvent tank 341. The S5 solvent from solvent tank 341 can be added to the plug flow reactor 313 using pump 342 situated between the solvent tank 341 and the plug flow reactor 313.

The mixture in the sugar mixture tank 311 and the solvent from solvent tank 341 can be contacted before entering the plug flow or in the plug flow reactor. In one instance, as depicted by FIG. 3, the outlet conduit leading the mixture from the sugar mixture tank 311 to the plug flow reactor 313 intersects with the outlet conduit of solvent tank 341 upstream of the plug flow reactor inlet.

In some embodiments, the S5 solvent in solvent tank 341 is maintained at a temperature greater than 140, 150, 160, 170, 180, 190, 200, 210, or 220° C. or between 145 to 180° C. In some instances, the stream of S5 solvent is heated through a flow heat exchanger to a temperature in the range of any of the temperatures described herein or 220-240° C. or 230-235° C. before contacting the solvent with the mixture (e.g., aqueous sugar stream).

Surprisingly, it was found that the heat up time of the reaction in the reactor (i.e. plug flow reactor) can impact the amount of undesired byproduct formed in the reactor. In a preferred embodiment the heat up time of the reaction mixture is shortened to a minimum by pre-heating the solvent to the reaction temperature. Preferably, the reaction conditions in the reactor such as the plug flow reactor 13 result in a conversion of the hemicellulose sugars at a rate of at least 80%, 81%, 82%, 83%, 84%, 85%, 86%, 87%, 88%, 89% or 90% of all C5 sugars in the aqueous sugar mixture entering into the plug flow reactor 313 (wt/wt DS). In one embodiment shown in FIG. 3, the aqueous phase is not recycled, but rather sent to waste (see 381 and 276). This can be beneficial in cases wherein the hemicellulose sugars (before being contacted with the acid, e.g., 1837-A or 1836) comprise a minimal amount of C6 sugars, such as up to 22%, 20%, 15%, 10%, 5%, or 3%, (wt/wt DS) C6 sugars. In such cases, at least a portion of the hexoses are expected to dehydrate to HMF. However, given the higher hydrophilicity of HMF as compared to furfural, much of the HMF is expected to remain in the aqueous phase along with any unreacted sugar, and can lead to decreased yields if recycled. Therefore, recycling can be less beneficial.

In some cases, the aqueous phase in the system (e.g., 302, 304, 350, 376 and/or 371) comprises a metal halide or alkaline metal halide salt at concentration of 0.5-10%. In some cases, the aqueous phase in the system comprises a metal halide or alkaline metal halide salt at concentration of 3-7% wt/wt. The aqueous phase in the system can comprise a metal halide or alkaline metal halide salt at concentration of up to 3, 4, 5, 6, 7, 8, 9, or 10% wt/wt. The aqueous phase in the system can comprise a metal halide or alkaline metal halide salt at concentration of at least 0.1, 0.2, 0.3, 0.4, 0.5, 0.6, 0.7, 0.8, 0.9, 1.0, 1.5, 2.0, 2.5, or 3.0% wt/wt. In this embodiment, or any other embodiment herein, the salt can be one that is selected from the group consisting of NaCl, NaBr, NaI, KCl, KBr, KI, $CaCl_2$, $FeCl_3$ and $AlCl_3$.

In some embodiments, a sugar composition comprising hemicellulose sugars (e.g., 1837-A) is used as feed for this system. The optimal sugar or hemicellulose sugar concentration prior to contact with the acid and/or base is preferably at least 1, 2, 3, 4, 5, 6, 7, 8, 9, or 10% wt/wt. Alternatively, or in combination, the optimal sugar or hemicellulose sugar concentration can be less than 1, 2, 3, 4, 5, 6, 7, 8, 9, or 10% wt/wt. In some cases the optimal sugar or hemicellulose sugar concentration can be between 1% and 10% inclusive wt/wt. The systems herein can adjust the concentration of the hemicellulose sugars. In some cases, the concentration of the hemicellulose sugar solution is increased by evaporation. If evaporation occurs after refining, there is minimal or no additional concentration required, thus reducing cost of production of the sugar mix. For example, the concentration of hemicellulose sugars in an SSMB effluent stream such as the one described in PCT/US2013/039585 can be 20-25% wt/wt. In such cases, some evaluation will be needed. In other cases, no evaporation is required but rather some dilution. In a preferred embodiment, the concentration of the sugar in the feed solution is 5-7%. Mineral acid (for example, $H_2SO_4$, HCl, etc.) is added to or mixed with the pentose solution in an amount sufficient to make the final reaction mixture have an acid normality of between 0.05 and 2. The acid may be added to the reactor directly or as shown to the pentose solution before it enters the reactor.

The aqueous sugar stream 304 and the organic solvent stream 344 can be fed in a manner such that they mix to form reaction mixture 333 and pass through the plug flow reactor 313 in a plug flow manner. This can take advantage of the high initial concentration of the C5 sugars. The concentration of the sugars can decrease as the mixture of solutions flows through the reactor 313. The reactor 313 can be operated in a manner such that the temperature of the reaction is at least 170, 180, 185, 190, 200, 205, 210, 220, 230, 240, 250, 275 or 300° C. In some cases, the reaction temperature is about 170° C. In some cases, the reaction temperature is maintained at about 195-205° C. The residence time of the hemicellulose sugars in the reactor 313 can be between 0.5 and 600 seconds, 50-300 seconds, 100-250 seconds, 190-210 seconds, or about 200 seconds. These numbers can be actual numbers or average numbers. The length of the reactor and/or the flow rate can be varied to obtain the desired residence (reaction) time. The reactor can be operated in essentially an isothermal manner. The reactants may be heated in any known manner, such as, steam coils, steam jackets or the like. Alternatively, the reactor may be any other kind of continuous reactor. The reactor 313 can be set under pressure that is above atmospheric pressure and high enough to prevent vaporization of the aqueous solutions. In some instances, the reactor is set at a pressure between 500 and 1500 psi.

The reactor temperature, residence time (e.g., flow rate) and pressure can be controlled by a reaction control unit as is described herein.

In a preferred embodiment, the organic solvent in the solvent tank 341 is an S5 solvent. While the reaction mixture 333 is in the reactor 313, at least a portion of the furfural is extracted into the solvent phase and is removed from the acid catalyst-containing aqueous phase. This increases furfural selectivity at the residence times necessary to obtain high furfural yields without the necessity of recycling unreacted pentose.

In FIG. 3, the reactor is operated in conjunction with decanter 344 and distillation column 345. Accordingly, the reactor 313 effluent is depressurized, cooled at heat exchanger 319, and fed into decanter 344 wherein the water and furfural-solvent phases are separated by gravity. In the illustration, the solvent phase has a density lower than the density of the water phase. In some embodiments, before entering the centrifuge the reaction effluent is filtered to remove any solids form in the reaction.

The furfural-enriched organic phase is heated up in heat exchanger 320 and fed into distillation column 345. Optionally, heat exchanger 319 and 320 are the same unit (i.e., one heat exchanger) that is used to cool reactor effluent (i.e., biphasic reaction mixture 333 exiting the plug flow reactor 313) and heat the furfural-enriched organic stream 344. This allows for optimizing energy utilization of the overall process.

At the distillation apparatus 345, furfural is distilled off the top while the solvent is collected at the bottom as the furfural-depleted organic stream 346. The top stream of isolated furfural 344 can have a purity greater than 90%, 92%, 95%, 97%, 99%, while the solvent stream at the bottom of distillation 345 (i.e., the furfural-depleted organic stream 346) has a residual amount of furfural (e.g., up to 3%, 2%, 1%, 0.5%, 0.1% furfural). In some embodiments, the furfural in the furfural-depleted organic stream 346 comprises at least 50 ppb of a marker molecule selected from the group consisting of: S5 solvent, chlorinated furan molecules, e.g. 5-chloromethylfuran-2-carbaldehyde, formic acid, levulinic acid, acetic acid, 5,5'-Diformyl-2,2'-difuran, HMF, and HCl.

Typically, distillation column 345 is maintained at a temperature of about 160° C. to about 170° C. at the top, and about 185° C. to about 195° C. at the bottom. The furfural-depleted organic stream 346 is cooled at heat exchanger(s) 321 and/or 322. In some instances, the furfural-depleted organic stream is cooled to 40-80° C. or 50-70° C. The excess heat at these heat exchangers can be used to reheat the recycled intermediate organic stream 390.

Surprisingly, it was found that the furfural-depleted organic solvent 346 can be effectively washed with a base and water solution 369 to remove byproducts 371 using decanter 370. The addition of a base can be used to bring the pH of the furfural-depleted organic stream 346 up to greater than 10.0, 10.5, 11.0, 11.5. The furfural depleted organic stream 346 is then washed by adding base and water 369 to an organic: aqueous ratio in the range of 0.5 to 4. The two phases are separated in a decanter 370. Aqueous phase 371 is collected at the bottom and comprises hydroxymethyl furfural (HMF) formed from dehydration of the C6 sugars present in the furfural depleted organic stream 346. This aqueous HMF stream 371 is optionally directed to a recovery system to recover HMF as a byproduct. The purified/return organic stream 373 is directed to centrifugal extractor 375 to extract and recover residual amounts of furfural that were not extracted into the solvent at reactor 313 and decanter 344. It was found that this second extraction can be effective enough to up to 1000, 500, 350, 100, 50, 10, or 5 ppm furfural in the furfural-depleted aqueous phase 376 exiting the system.

From the centrifugal extractor 375, the solvent is recycled back into the feed of the distillation column via the intermediate organic stream 390 to recover furfural by distillation. Existing furfural depleted aqueous stream 376 is essentially free of furfural and may be used to dilute the feed stream of sugar mix or any other dilution stream needed in the system. Alternatively is may be directed to the waste treatment unit of the plant.

The intermediate aqueous stream 350 leaving decanter 344 is optionally directed to a mechanical vapor recompression (MVR) striper 380 to concentrate the furfural product by up to 5, 6, 7, 8, 9, or 10 fold by removing water 381. Preferably, prior to entering the MVR stripper 380, base 369 is added to the solution to bring the pH up to at least 4.5, 5, 6, or 7. This can minimize degradation of the furfural during water evaporation. The aqueous phase is then fed into a centrifugal extractor 375 where it is extracted with the purified/return organic stream to extract furfural that remained in the aqueous phase at the first separation in decanter 344.

Figure 4:
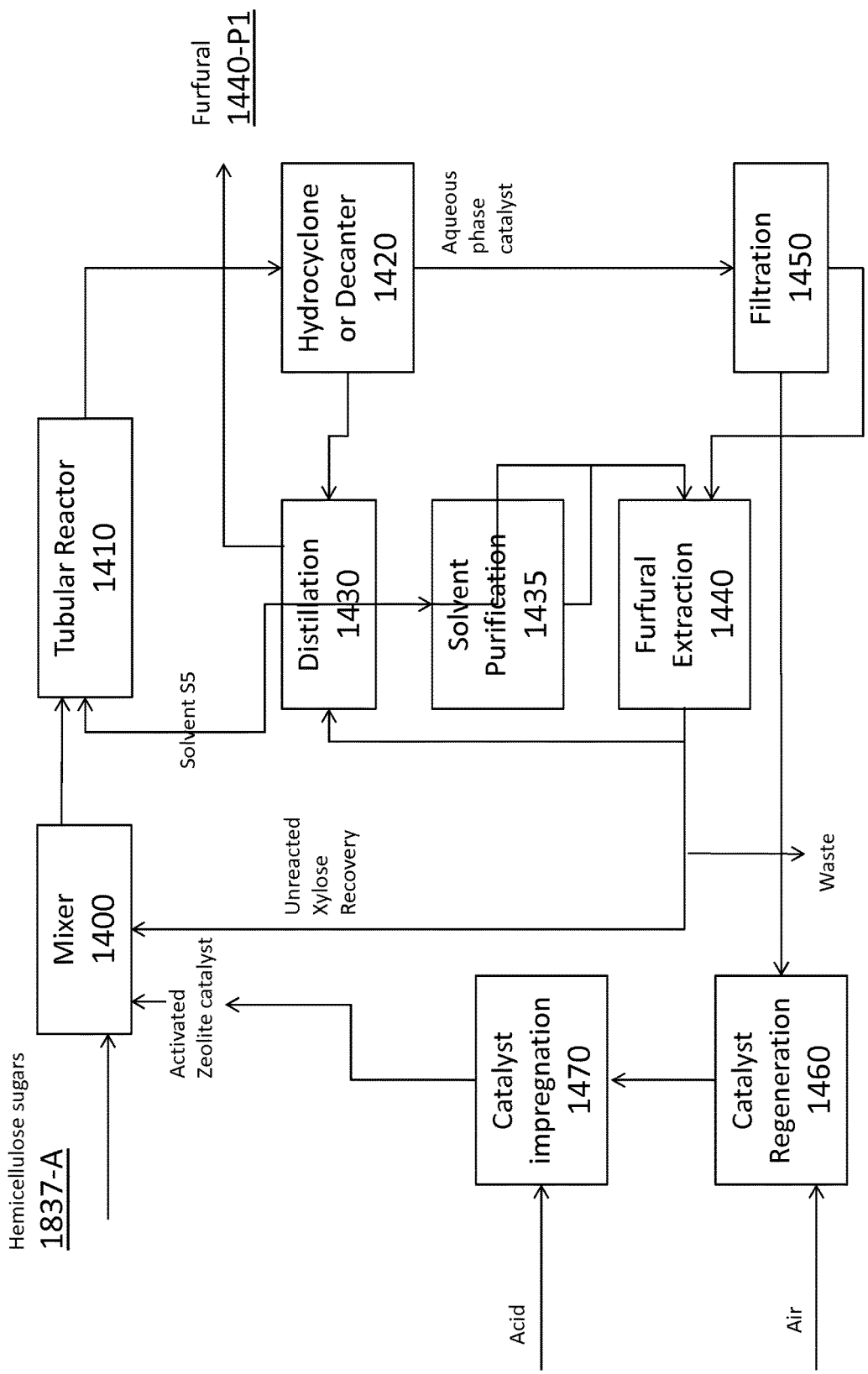
FIG. 4 shows a flow scheme for conversion of a predominantly C5 sugar mix to predominantly furfural by catalytic dehydration.

A system for the dehydration of hemicellulose sugars to furfural using a solid catalyst (e.g. zeolite) is presented schematically in FIG. 4. The concentration of sugar in the hemicellulose sugar mixture 1837-A is adjusted by water evaporation or dilution with water such that the final concentration of the sugar or hemicellulose sugar is 3-40%, 5-25%, 6-13% wt/wt. The aqueous hemicellulose sugar stream is mixed in mixer 1400 with an activated mineral zeolite catalyst. The ratio of catalyst to sugar in the sugar mixture can be between 0.2 to 5, 0.5 to 4, 1 to 3, or 1.5 to 2.5% wt/wt. This aqueous slurry is emulsified with an organic solvent (e.g. S5 solvent) in a tubular reactor 1410 that is operably connected downstream of the mixer 1400. Emulsification occurs by a high shear mixer in the tubular reactor 1410 or a static mixer or any other industrial mixer suitable for making an emulsion of S5 solvent and the aqueous hemicellulose sugar stream. Preferably, the ratio of the organic solvent to the aqueous solution in the tubular reactor 1410 is at least 5:1, 4:1, 3:1, 2:1, 1:1, or 0.5:1 (wt/wt) or (vol/vol) or about 5:1, 4:1, 3:1, 2:1, 1:1, or 0.5:1 (vol/vol). The resulting emulsion is then made to flow through a tubular reactor 1410, e.g. a plug flow reactor, heated to 150-180° C., 200-300° C., 220-280° C., 250-270° C., 255-265° C., under 50-60 atm. nitrogen pressure. In one method, as depicted in FIG. 4, the mixing is done in the tubular reactor, where the tubular flow reactor is constructed so as to cause mixing of the incoming streams. The flow and reactor size are controlled such that the residence time in the reactor is 0.5 seconds to 10 min, 2.0 min to 7 min, 2.5 min to 5 min, or 2.8 min to 3.2 min. Furfural has high affinity to S5 solvent, and is extracted into the organic phase at more than 88%, or more than 90%, 93% 95%, 96%, 97% or 98% efficiency, consequently removing it from the aqueous phase where it may continue to react to form side products in the presence of the acidic catalyst. The S5 solvent is selected such that furfural partitions preferable into the solvent.

The emulsion coming out of the mixer/tubular reactor 1410 comprises an organic phase comprising furfural, an S5 solvent, and S5 solvent-soluble byproducts, and an aqueous phase comprising HMF, any unreacted sugars, salts, water-soluble byproducts and the suspended zeolite particles.

The out-coming emulsion is made to flow through a heat exchanger to cool down, and is then separated to organic phase and an aqueous phase by decantation or by hydrocyclone 1420, or by any other suitable means to separate phases. In one embodiment, same heat exchanger may be used to transfer heat from the outgoing emulsion to the incoming aqueous phase prior to emulsification with S5 solvent.

The catalyst utilized in the embodiments represented by FIG. 4 can be one that is selected from a group consisting of: zeolite SM-25, mordenite, faujasite, H-ferrierite, H-β, H-ZSM-5, H-Y, silica-alumina, and mesoporous molecular sieve MCM-41, wherein the silica to alumina ratio is from about 5:1 to about 500:1. Alternatively or in combination the catalyst may be $HTiNbO_5$—MgO, or $ZrO_2$—$Al_2O$.

The catalyst is impregnated 1470 with acid prior to use by suspending it in water and acidifying it to pH 2.3-2.5. This acidification may be done with a strong acid such as, for example, one that is selected from HCl, $H_3SO_4$, $H_2SO_4$, and H$_3$PO$_4$. The catalyst is regenerated 1460 between cycles through wet oxidation by heating it to temperature higher than 180, 190, 200° C. for at least 60, 120, 180 minutes in a stirred pressurized tank (Top. Catal. (2010) 53:1231-1234, Kor. J. Chem. Eng. (2011) 28(3):710-716).

The systems described herein can be operable on a continuous basis. Alternatively or in combination, the system can be operable on a batch-wise basis.

The systems described herein can comprise at least one recycling loop. A recycling loop can be a system of chambers, pipes, solvent flow channels, or the like, wherein the loop forms a cyclical system. In some cases, the system can comprise at least 2 recycling loops. For example, the system can comprise an aqueous solution recycling loop and an organic solvent recycling loop. In some cases, systems comprise at least 3 continuous loops. In cases wherein the system comprises at least 3 loops, 2 or more continuous loops can be organic solvent recycling loops. The continuous loops of the system can reduce the amount of solvent waste or aqueous waste the system produces per day.

The systems described herein can produce at least 1.0 tons of furfural for each 2.3 tons of hemicellulose sugars provided, wherein the hemicellulose sugars comprise at least 80% xylose (by weight) and wherein the system is configured for processing at least 1.1 tons of hemicellulose sugars per day.

The systems can be configured to produce furfural on an industrial scale, e.g., at least 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.5, 3.0, 3.5, 4.0, 5.0, 6.0, 7.0, 8.0, 9.0, or 10.0 tons of furfural per day. The furfural produced can be in the form of an isolated furfural stream. For example, the furfural can be stream 230 or 1440-P1 in FIG. 2.

The systems can be configured to generate either none or a small amount of organic solvent waste. For example, the system can be configured to generate less than 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, or 1.0 ton of organic solvent waste per day. The system can be configured to produce an amount of organic solvent waste per day that is less than 10, 9, 8, 7, 6, 5, 4, 3, 2, 1, 0.5 or 0.1% of the amount of furfural produced per day (wt/wt). In some cases, the system is configured to generate less than 0.01 ton of organic waste per day and at least 1.0 ton of furfural per day. The organic waste 240 can be purged from an organic stream such as the stream between 145 and 141 in FIG. 2. In some embodiments, no organic waste is purged from the system. For example, the only organic solvent that leaves the system is an amount of solvent that partitions into the aqueous phase through the extraction processes described herein.

The systems can be configured to generate a relatively small amount of aqueous waste per day. For example, the system can be configured to generate less than 40, 30, 20, 10, 9, 8, 7, 6, 5, or 4 tons of aqueous waste per day. The system can be configured to produce an amount of aqueous waste per day that is less than 100, 90, 80, 70, 60, 50, 40 30, 20, 10, 5, 2, 1, or 0.5 times the amount of furfural produced per day (wt/wt). In some cases, the system is configured to generate less than 20 tons of aqueous waste per day and at least 1.0 ton of furfural per day. The aqueous waste can be purged from the system from 170 or 180 in FIG. 2.

The systems and methods herein provide for an enhanced conversion of xylose and have a xylose conversion percentage greater than 50, 60, 70, 80, 90, 95, 99, or 99.5%. A conversion percentage of xylose is defined by how much xylose is chemically reacted to produce other products. The systems and methods herein also have an enhanced selectively in converting to furfural. Selectivity percentage for the system is defined as what percentage of the reacted pentose (e.g., xylose and/or aribinose) forms furfural. Thus, the systems and methods herein provide for conversion of C5 sugars (e.g., xylose) to furfural with a selectivity of greater than 50, 60, 70, 80, 85, 90, 95, 99, or 99.5%.

The system can produce an isolated furfural product 1440-P1, wherein the furfural is isolated as a substantially pure product. For example, the isolated furfural can be at least 70, 80, 90, 95, 99, or 99.9% pure.

Compositions of the Systems, Methods and Processes.

Provided herein is a composition comprising: at least 90% furfural by weight; water in an amount up to 5% by weight; S5 solvent in amount up to 1% by weight; and at least two impurities, wherein the total amount of all impurities together is up to 5000 ppm by weight relative to furfural; wherein the impurities are selected from the group consisting of formic acid, levulinic acid, acetic acid, 5-chloromethylfuran-2-carbaldehyde, 5,5'-diformyl-2,2'-difuran, HMF, and HCl. In some cases, the composition comprises at least 95, 96, 97, 98, 99, 99.9% furfural, wherein water amount is less than 1% and S5 amount is less than 0.1%. The S5 solvent can be tetralin. In some cases, the composition comprises HMF and diformyl-2,2'-difuran.

Further provided herein is a composition comprising: at least 95% tetralin by weight; at least two impurities, wherein the total amount of all impurities together is up to 2% by weight relative to tetralin; wherein the impurities are selected from the group consisting of furfural, water, HMF, HCl, NaCl, formic acid, levulinic acid, acetic acid, 5-chloromethylfuran-2-carbaldehyde, 5,5'-diformyl-2,2'-difuran,5-(furan-2-yl-hydroxy-methoxymethyl)-furan-2-carbaldehyde, humins, cis-decalin, trans-decalin, naphthalene, and polyfurfural species.

Also provided herein is a composition comprising: an aqueous solution comprising about 5% NaCl, 0.3-2% HCl, HMF, furfural, S5 solvent, xylose, arabinose, glucose, levulinic acid, and formic acid.

2. Chemical Conversion of Furfural to High Value Products

Furfural produced in this process is suitable for many further conversions to a wide spectrum of high value chemicals, including but not limiting to furfuryl alcohol, 2-methyl furan, tetrahydrofuran (THF), various organic acids such as succinic acid.

Furfural offers alternative ways for producing numerous materials as well as new generation biofuels. Potential and upcoming markets for furan resins cover a wide spectrum with massive potential utilization, from wood preservatives to construction materials. In the past furfural has been already used as starting material for the production of important chemical intermediates like THF. Favorable balances between oil prices and furfural availability, as well as green oriented policies, are likely to drive a switch back to the furfural based routes.

As far as the energy sector is concerned, direct hydrogenation derivatives of furfural also have a high potential as alternative liquid fuels and fuel extenders. 2-Methyltetrahydrofuran (MTHF) has been proven to show superior characteristics as fuel extender in regular gasoline, as well as in alternative fuels formulations based on ethanol (P-series fuels). 2-Methylfuran and tetrahydrofurfurylalcohol (THFA) could also be potential candidates as biomass derived octane enhancer, and as diesel fuel additive. Furthermore, by controlled reactions involving furfural, such as aldol condensation, alkylation and etherification, larger molecules may be obtained, that can undergo subsequent hydrogenation/hydrogenolysis to molecules with superior fuel characteristics, such as higher alkanes (see, e.g., WO2012057625; the content of which is incorporated herein by reference).

3. Oxidation of Furfural to Maleic Acid and Succinic Acid

Succinic acid is a compound of high importance and applications as a building block for fuel additives, in polyurathans, as well as many applications as plasticizer, and as additive in food, cosmetic and pharma products. Succinic acid substitutes maleic anhydride in the production of commodity chemicals such as 1,4-butanediol. There is great interest in succinic acid from renewable source. Most processes being developed are based on fermentation, such process comprises growing an anaerobic succinate producing microorganism in a fermentor, in a medium comprising considerable amounts of carbon source, typically carbonate salts, as well as additional nutrients and carbohydrate, i.e., glucose, galactose, mannose, xylose as well as higher DP carbohydrates, under anaerobic conditions and partial pressure of $CO_2$, at pH suitable for microbial growth, typically 5-7. The isolation and refining of succinic acid from the resulting fermentation broth is complicated and costly, it is estimated that refining accounts for 60-70% of the production cost. Refining processes reported include precipitation, distillation, electrodialysis, extraction, reactive extraction, ion exchange. However, to achieve purity sufficient for crystallization and further use multiple refining steps are required, most associated with high cost.

Figure 5A:
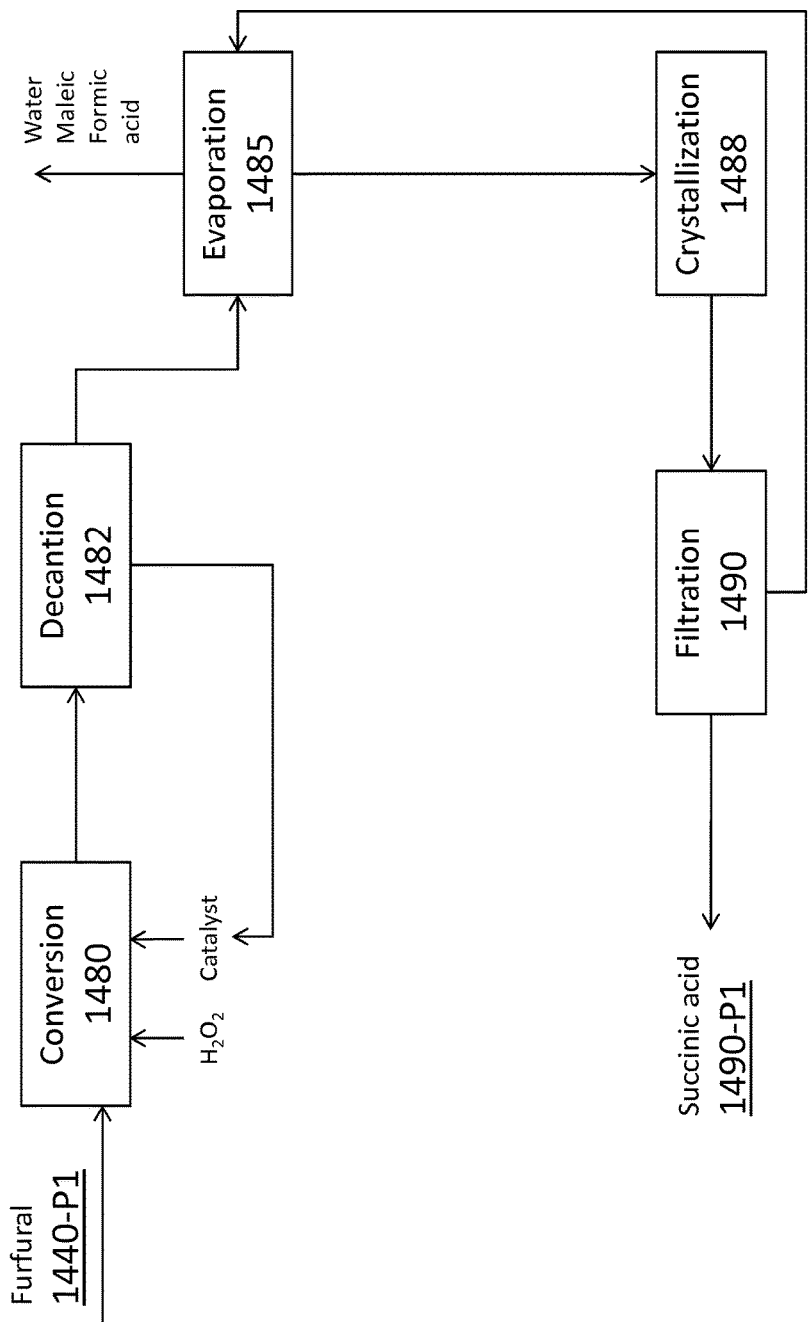
FIG. 5A shows a flow scheme for further conversion of furfural to succinic acid by catalytic oxidation and for the refining and crystallizing of succinic acid.
Figure 5B:
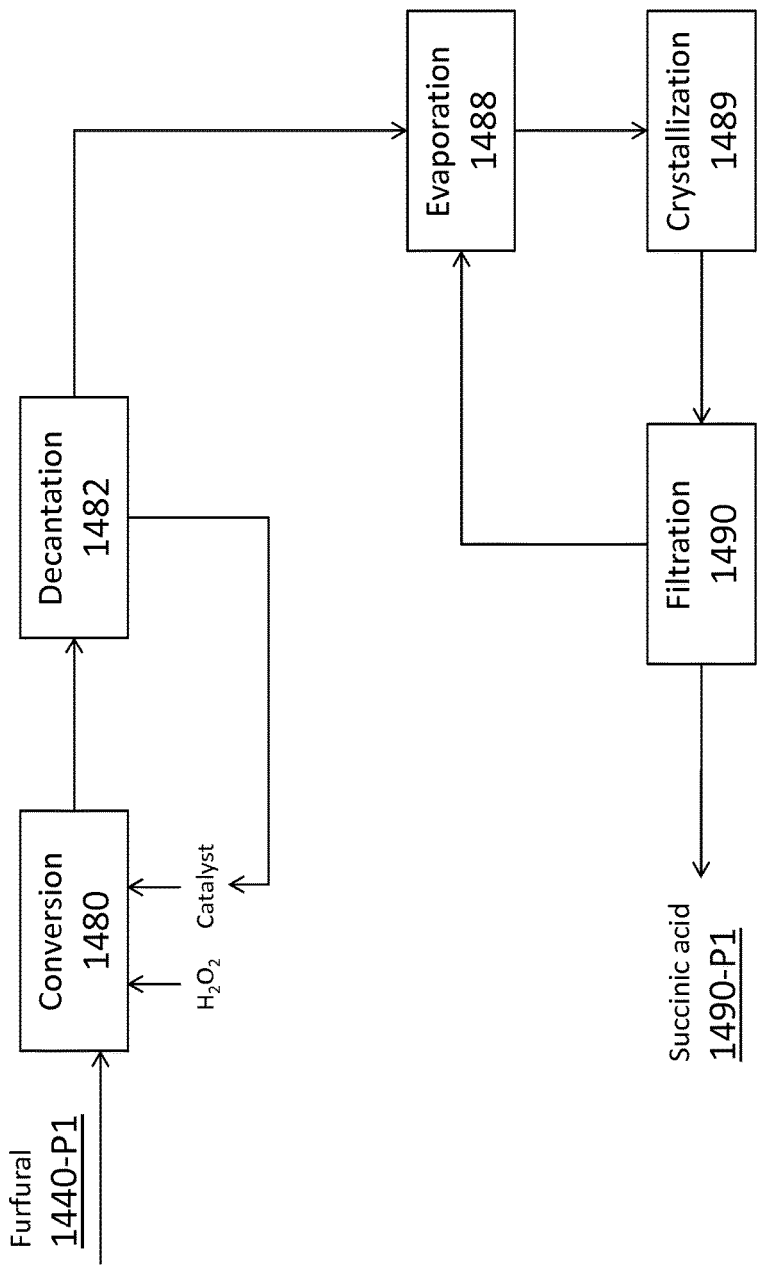
FIG. 5B shows a flow scheme for further conversion furfural to succinic acid.

FIGS. 5A and 5B are alternative schemes of a process for the conversion of furfural to succinic acid. Furfural is oxidized 1480 to succinic acid by reacting it with 30% $H_2O_2$ in water, in the presence of strongly acidic, sulfonic acid, macroreticular polymeric resin based on crosslinked styrene divinilbenzen copolymers. Such strongly acidic cationic ion exchanger may be purchased from Dow Chemical Company as Amberlist 15. The mixture is stirred at 60-120° C. for 1-30 h under ambient pressure. Yield of succinic acid is greater than 50%, 60%, or 70% while furfural conversion is greater than 90%, 95%, 97%, or 99%. By products formed include fumaric acid, maleic acid and/or furoic acid (see, e.g., JP 2013126967, Chemistry Letters (2012), 41(4), 409-411; the contents of which are incorporated herein by reference).

Other strong acid solid catalyst me be applied, including Amberlyst Nafion® NR50, Nafion® SAC13, Apetite FAP hexaclinic.a zeolite, silica-alumina, sulfated zirconia, sulfated carbon, or any combination thereof.

The solid catalyst is recovered by filtration or decantation 1482 and recycled for further reactions. The reaction mixture is evaporated at 50-60° C. under reduced pressure 1485, water, maleic acid and formic acid are effectively removed. The solution is concentrated to greater than 30%, 40%, 50%, 60%, 70%, or 80% and succinic acid is crystallized. Crystallization 1488 of succinic acid is induced by lowering the temperature of the solution, and optionally by seeding and/or optionally by adding anti solvent and/or optionally applying vacuum. The yield of crystalline succinic acid relative to furfural is greater than 50%, 55%' 60%, or 65%. The crystals are collected by filtration 1490, washed with water and dried.

4. Reduction of Furfural to Furfuryl Alcohol.

Furfuryl alcohol is a valuable chemical reagent for numerous conversion. The hydrogenation of furfural (furaldehyde) to the alcohol requires control of catalyst and conditions to achieve specificity. The reduction of the C=O bond in a ketone or aldehyde functional group to the corresponding alcohol is one of the fundamental reactions in organic chemistry, and is used in a large number of chemical processes. In general, three kinds of processes are known to achieve such a transformation:

a) hydride processes, in which a silyl or metal hydride salt, such as $LiAlH_4$, or PMHS (polymethylhydrosiloxane) is used;

b) hydrogen transfer processes, in which a dihydrogen donor (such as HCOOH or 'PrOH) is used;

c) direct hydrogenation processes, in which molecular hydrogen is used (see, e.g., WO2012084810, the content of which is incorporated herein by reference).

Furfural is optionally vacuum distilled to remove oxidized condensation process. In one embodiment, hydrogenating is carried out at $H_2$ pressure 1.0-8.0 MPa and 90-160° C. in the presence of skeletal Cu catalyst and adjuvant to obtain furfuryl alcohol (see, e.g., CN102603681, the content of which is incorporated herein by reference). Alternatively the hydrogenation catalysis is Cu/Si, Cu/Cr or any combination thereof (see, e.g., CN101463021, the content of which is incorporated herein by reference).

In another embodiment, ethanol is used as a hydrogen donor by reacting furfural in ethanol for 2 hours at 110-150° C. in the presence of an amorphous alloy Ni-L-B catalyst (see, e.g., CN990476, the content of which is incorporated herein by reference).

5. Reduction of Furfural to 2-methyl furan 2-methyl furan is a valuable compound, used as fuel, octane enhancer, as well as reagent for numerous chemical conversions.

Furfural is hydrogenated by reacting it in a suitable solvent over a hydrogenation catalyst in the presence of hydrogen gas under pressure, typically 40-60 bar. The hydrogenation reaction is carried out at 70-200° C., preferably at 70-100° C. Palladium compounds are particularly suitable as catalysts for this hydrogenation, preferred compound for industrial use is palladium on activated carbon. Other palladium catalyst may also be used. Alternatively, such catalyst may comprise Pt, Ru, Cu, Rh or other metal compounds. Suitable solvent may be water, alcohol, acetonitrile, ionic liquid, and mixtures thereof.

6. Conversion of Furfural to Tetrahydrofuran

Tetrahydrofuran (THF) is a cyclic ether with several industrial uses. The major use is as a monomer in the production of polytetramethylene ether glycol (PTMEG), a component of cast and thermoplastic urethane elastomers, polyurethane stretch fibers (spandex) and high-performance copolyester-polyether elastomers. A smaller amount of THF is used as a solvent in polyvinyl chloride (PVC) cements, pharmaceuticals and coatings, in precision magnetic tape manufacture and as a reaction solvent. Currently, THF is manufactured predominantly by the method of 1,4-butanediol (BDO) cyclization. Emerging technologies propose the production of BDO via fermentation of sugars to obtain succinic acid with the consecutive conversion to BDO, or directly by fermentation of sugars. However, THF can be produced in a two step reaction by direct conversion of furfural: (i) decarbonylation of furfural to furan; (ii) hydrogenration of furan to THF.

Figure 6A:
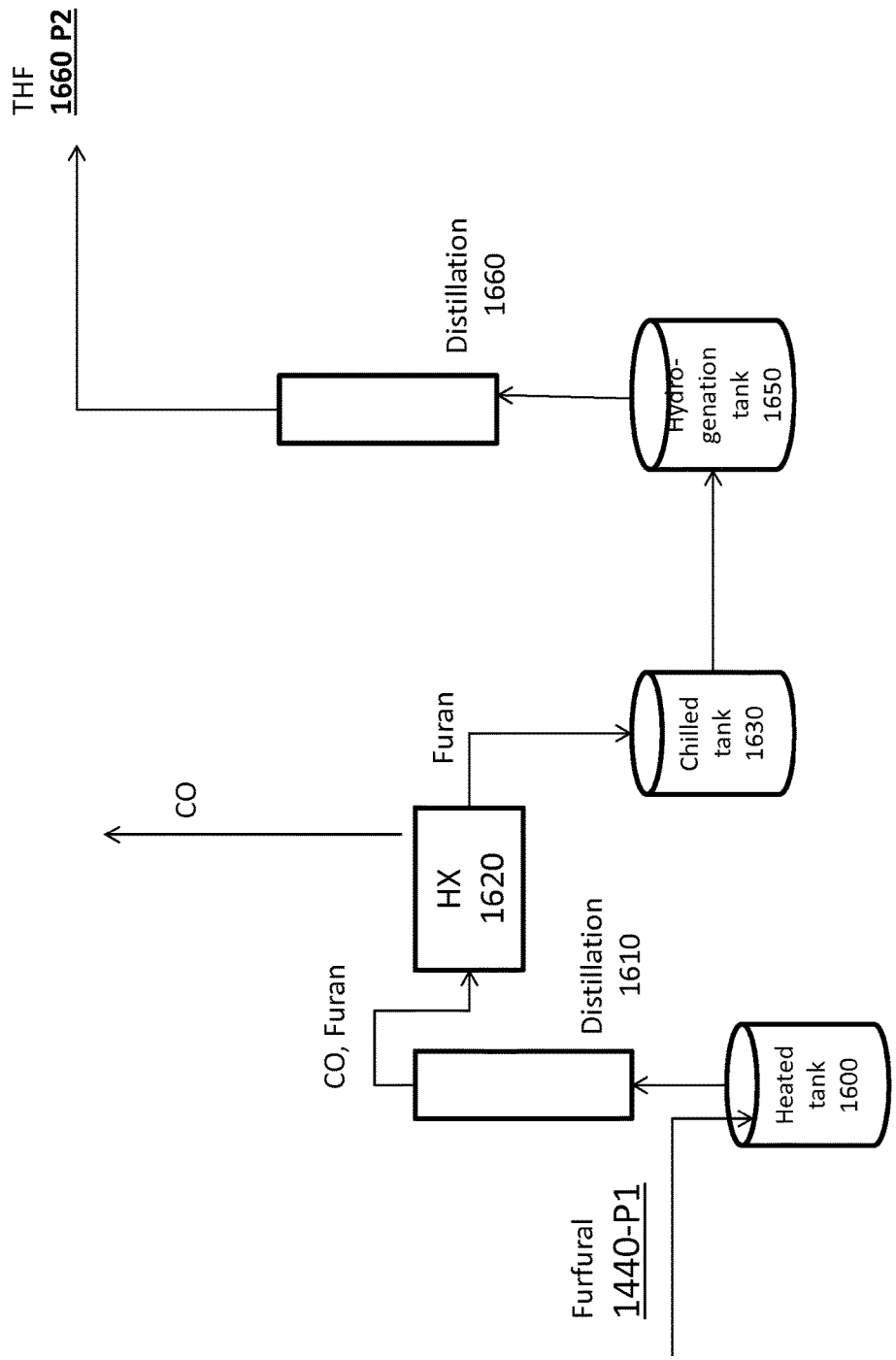
FIG. 6A shows a flow scheme for converting furfural to THF.
Figure 6B:
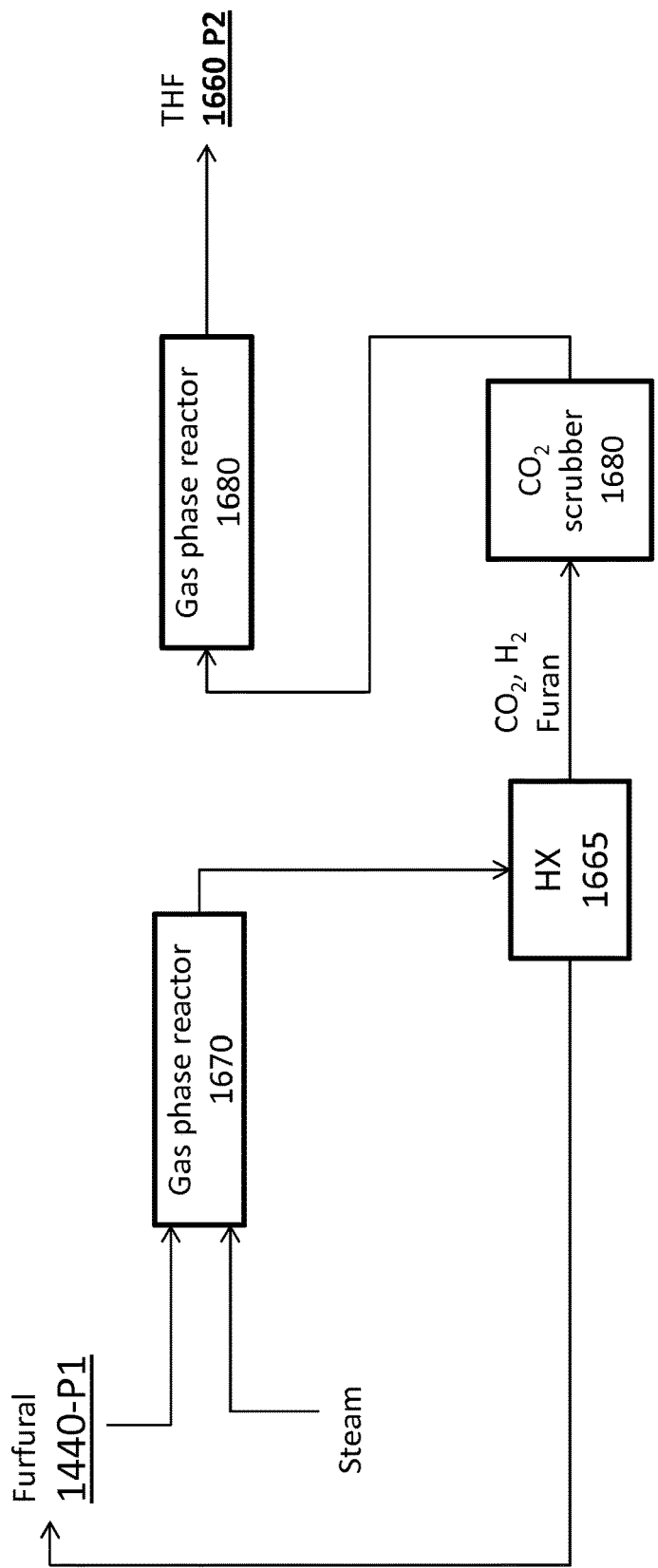
FIG. 6B shows an alternative flow scheme for converting furfural to THF.

Processes for the stepwise conversion of furfural to THF are outlined schematically in FIG. 6A for liquid phase conversions and FIG. 6B for gas phase conversions. Furfural may be decarbonylated to furan either in the liquid phase with an appropriate catalyst but boiling furfural or furfural in a solvent. Alternatively, the process may be carried out in the gas phase. In both cases heterogeneous catalysts are used. Catalysts known to catalyze the decarbonylation of furfural to furan include but are not limited to Mn chromites, Zinc molibdate, copper molibdate, oxides of Zn, Cr, Mn, Al and their mixed oxides, Ni alloy catalysts, Ni/C, Ni/Cr oxide, Raney Ni, Al—Zn—Fe catalysts, Pd, Pt, Rh, Ru or Mo supported over carbon, silica, alumina, or various zeolites. Optionally, a basic salt is added as enhancer that extends catalyst life. Suitable salts include $K_2CO_3$ and other alkali carbonates. The effluent is separated by distillation: unreacted furfural is condensed and returned for further reaction, while furan, CO or $CO_2$ and $H_2$ are collected at the head. The stream is contacted with base to remove $CO_2$.

The resulting furan is hydrogenated either in liquid phase or in the gas phase in the presence of hydrogenation catalysts. The source of hydrogen may be the $H_2$ released in the first stage, additional supply of $H_2$ or alternatively a hydrogen donor, such as formic acid, ethanol or isopropanol.

To utilize the energy stored in organic solutes and to comply with environmental requirements, aqueous waste streams that contain organic matter can be treated in anaerobic digesters to produce methane, which can be burned. However, anaerobic digesters are known to be poisoned by too high levels of sulfate ions per a given chemical oxygen demand (COD) level, and can be limited to the incoming stream having less than 400 ppm calcium ions to prevent calcium carbonate build up in the digester. The aqueous waste streams produced as described herein can comply with these requirements. Furthermore, as disclosed above, back extraction may be conducted in several steps allowing better control of the inorganic ion level versus the organic matter.

EXAMPLES

It is understood that the examples and embodiments described herein are for illustrative purposes only and are not intended to limit the scope of the claimed invention. It is also understood that various modifications or changes in light the examples and embodiments described herein will be suggested to persons skilled in the art and are to be included within the spirit and purview of this application and scope of the appended claims. All publications, patents, and patent applications cited herein are hereby incorporated by reference in their entirety for all purposes.

Example 1—Analysis of a C5 Hemicellulose Sugar Stream 1837-A Suitable for Conversion to Furfural A xylose-rich extract stream was generated by extraction of hemicellulose in addition to refining and enrichment of xylose by SSMB according to PCT/US2013/039585 (incorporated by reference herein). The extract was analyzed for carbohydrate concentration, composition and impurity profile. This stream comprises a high concentration of C5 sugars, predominantly xylose, and very low impurity levels, which make it exceptionally suitable feed for catalytic conversion to furfural.

TABLE 1

Carbohydrate composition of C5 sugar stream suitable for conversion to furfural

| Parameter | Result | Units |
|---|---|---|
| Appearance | Colorless | |
| pH | 3.58 | |
| Saccharides | | |
| % TS (HPLC) | 68.2 | % w/w |
| Composition (HPAE-PAD) | | |
| Xylose | 81.84 (55.81) | %/TS (% w/w) |
| Arabinose | 4.38 (2.99) | %/TS (% w/w) |

TABLE 1-continued

Carbohydrate composition of C5 sugar stream suitable for conversion to furfural

| | Result | Units |
|---|---|---|
| Mannose | 1.99 (1.36) | %/TS (% w/w) |
| Glucose | 5.07 (3.46) | %/TS (% w/w) |
| Galactose | 0.91 (0.62) | %/TS (% w/w) |
| Fructose | 6.15 (4.20) | %/TS (% w/w) |
| Impurities | | |
| Furfurals (GC) | <0.005 | % w/w |
| Phenols (FC) | 0.04 | % w/w |
| Metals & inorganics (ICP) | | |
| Ca | <2 | ppm |
| Cu | <2 | ppm |
| Fe | <2 | ppm |
| K | <2 | ppm |
| Mg | <2 | ppm |
| Mn | <2 | ppm |
| Na | <2 | ppm |
| S | <10 | ppm |
| P | <10 | ppm |

Example 2: Conversion of Xylose to Furfural in a Biphasic System

Experiments were conducted in a lab-scale plug flow reactor comprising a Koflo, Part No. 1/2-32 Stratos Static Tube Mixer, having a 24¾" long×0.43" ID, 316L SS static mixture tube. Feed solutions were fed using two HPLC preparatory pumps (SSI Prep 100). The system utilized a combination of a hot silicone oil bath and NT7076 coiled cable heaters, ½" ID×12.25" long, at 240V and 1300 W, with internal type J thermocouples.

$H_2SO_4$ was added at 0.1 normality to an aqueous solution of xylose (6% xylose w/w %). All experiments were conducted using 1,2,3,4-tetrahydronaphthalene (tetralin) as the organic solvent. Both phases were added to a feed tank and sufficiently agitated to maintain a uniform emulsion throughout the duration of the experiment. The ratio volume/volume of organic to aqueous (O:A) solutions was selected from 1:1, 2:1 or 1:2. The feed was then introduced to the reactor system using the HPLC pumps at rates dictated by residence time, τ (seconds). Residence times of τ=25 s, τ=30 s, τ=45 s, τ=60 s, and τ=90 s required a net flow rate through the system of 132 ml/min, 110 ml/min, 73 ml/min, 55 ml/min, and 37 ml/min, respectively. When the system stabilized at the appropriate temperature, a full system volume was purged ($V_{system}$=280 ml), at which point 350-500 ml of reactor effluent was collected in 1 L bottles for analysis. Organic products were analyzed using gas chromatography with an FID, and a ZB-WAX plus column of 30 m length×0.25 mm ID×0.25 μm film thickness. Aqueous products were analyzed using high performance liquid chromatography (HPLC) with a refractive index detector and an aminex 87-H column. Results of various runs are summarized in Table 2.

TABLE 2

Conversion of xylose to furfural in a biphasic system

| Temp [° F.] | τ [sec] | O:A | Conversion [%] | Selectivity [%] | Yield [mol %] | Yield [w/w %] |
|---|---|---|---|---|---|---|
| 475 | 30 | 1:1 | 93 | 79 | 73 | 47 |
| 475 | 30 | 2:1 | 98 | 77 | 75 | 48 |

TABLE 2-continued

Conversion of xylose to furfural in a biphasic system

| Temp [° F.] | τ [sec] | O:A | Conversion [%] | Selectivity [%] | Yield [mol %] | Yield [w/w %] |
|---|---|---|---|---|---|---|
| 475 | 30 | 1:2 | 87 | 78 | 68 | 43 |
| 375 | 30 | 1:1 | 24 | 49 | 12 | 8 |
| 400 | 30 | 1:1 | 48 | 63 | 30 | 19 |
| 425 | 30 | 1:1 | 70 | 74 | 52 | 33 |
| 450 | 30 | 1:1 | 94 | 79 | 74 | 47 |
| 475 | 30 | 1:1 | 99 | 76 | 75 | 48 |
| 375 | 45 | 1:1 | 49 | 58 | 28 | 18 |
| 400 | 45 | 1:1 | 78 | 62 | 49 | 31 |
| 425 | 45 | 1:1 | 96 | 63 | 61 | 39 |
| 450 | 45 | 1:1 | 99 | 62 | 61 | 39 |
| 475 | 45 | 1:1 | 99 | 60 | 59 | 38 |
| 375 | 60 | 1:1 | 78 | 57 | 45 | 29 |
| 400 | 60 | 1:1 | 96 | 60 | 57 | 37 |
| 425 | 60 | 1:1 | 99 | 58 | 58 | 37 |
| 450 | 60 | 1:1 | 99 | 55 | 55 | 35 |
| 475 | 60 | 1:1 | 99 | 54 | 53 | 34 |
| 425 | 25 | 1:1 | 58 | 76 | 44 | 28 |
| 450 | 25 | 1:1 | 83 | 73 | 61 | 39 |
| 475 | 25 | 1:1 | 96 | 68 | 65 | 41 |
| 500 | 25 | 1:1 | 99 | 68 | 67 | 43 |

Example 3: Conversion of Xylose to Furfural in a Biphasic System

Experiments were conducted as described in Example 2. HCl was added at 0.2% to an aqueous solution of water, xylose (2% xylose w/w %) and NaCl (2-5%). All experiments were conducted using tetralin as the organic solvent at a ratio of organics:aqueous (O:A) of 1:1. The results are summarized in Table 3.

TABLE 3

Conversion of xylose to furfural in a biphasic system

| Temp [° F.] | τ [sec] | % NaCl | Conversion [%] | Selectivity [%] | Yield [mol %] | Yield [w/w %] |
|---|---|---|---|---|---|---|
| 392 | 200 | 5 | 87 | 89 | 78 | 50 |
| 392 | 400 | 5 | 85 | 90 | 76 | 49 |
| 392 | 200 | 5 | 73 | 89 | 65 | 42 |
| 392 | 200 | 2 | 74 | 78 | 58 | 37 |
| 392 | 100 | 2 | 50 | 76 | 38 | 24 |
| 392 | 60 | 2 | 30 | 76 | 30 | 19 |

Example 4: Recycling of the Organic Phase after Furfural Extraction

A mixture of tetralin loaded with furfural (approximately 2%) and additional by-products that were extracted during the reaction was heated to 95° C. for 3 hours. After 30 minutes, the color of the mixture darkened. The solution was then filtered through 20-25 micron filter paper. The apparent pH of the solution was adjusted to 11-13 by adding a 50% NaOH solution and water, to a ratio of organics:aqueous (O:A) of 1:1. The two phases were separated by decanting, after which, the organic phase was washed twice by adding fresh water and decanting. The residual amount of furfural in tetralin was 0.05-0.07% wt/wt, the resulting solution was clear and slightly yellow in color. Tetralin treated in this manner was found to be equally suitable for extracting furfural in the next cycle of the process as fresh tetralin.

Example 5: Furfural Extraction into Tetralin

The extraction of furfural into tetralin from 0.1N $H_2SO_4$ aqueous solution was conducted to determine the ratio of organic:aqueous (O:A) needed to remove 90% of the furfural in a given mixture in a single step. Solutions were mixed in a thermostated orbital shaker at the temperatures reported in Table 4 for 30 minutes. Samples were allowed to phase separate for 10 minutes, after which each phase was sampled for analysis by GC (organic phase) and HPLC (aqueous phase). The GC analysis was performed using an HP 5890 II analyzer using an ZB-WAX column (30 m length×0.25 mm ID×0.25 μm film thickness) using nitrogen as carrier, FID detection, a temperature gradient program of: 75° C., 10° C./min up to 150° C., 40° C./min up to 250° C. for 2 min. HPLC analysis was carried on an Agilent, 1100 series HPLC with a UV detector, a Bio-Rad Aminex HPX-87H 300×7.8 mm column, and an eluent of 0.005M $H_2SO_4$, at 1 ml/min and 65° C. The results are summarized in Table 4.

TABLE 4

Extraction of furfural into tetralin

| Furfural % wt | Glucose % Wt | $H_2SO_4$ N | pH (by NaOH addition) | O:A | Temp ° C. | % Furfural/O | % Furfural/A |
|---|---|---|---|---|---|---|---|
| 1.5 | 1 | 0.1 | 4.0 | 2 | 40 | 1.3 | 0.2 |
| 1.5 | 1 | 0.1 | 4.0 | 2 | 80 | 1.3 | 0.2 |
| 6 | 10 | 1 | 4.3 | 1.5 | 40 | 5.5 | 0.5 |
| 6 | 10 | 1 | 4.3 | 1.5 | 80 | 5.5 | 0.5 |
| 15* | 10 | 1 | 4.2 | 2 | 40 | 13.5 | 1.5 |
| 15* | 10 | 1 | 4.2 | 2 | 80 | 13.5 | 1.5 |

*some furfual is present as a seprate phase, as this amount is above the solubility in the aqueous phase.

The effect of temperature variations in the range tested is negligible. Tetralin extracts furfural from the aqueous phase to greater than 86% in all cases tested. The residue of furfual in the aqueous phase is lowest at the low concentration.

Example 6: Conversion of a C5 and C6 Sugar Mixture to Furfural

Experiments were conducted as described in Example 2. Table 5 summarizes concentrations of reactants, reaction conditions and the yields obtained for several sugar mixtures. All experiments were conducted using tetralin as the organic solvent.

TABLE 5

Conversion of a C5 and C6 sugar mix to furfural

| Xylose % wt/wt | Glucose % wt/wt | Arabinose % wt/wt | Mannose % wt/wt | Galactose % wt/wt | HCl % wt/wt | NaCl % wt/wt | O:A Wt/wt | Temperature (° C.) | Residence Time (s) | Conversion | Selectivity | Total Yield, %: | Total Yield, w/w %: |
|---|---|---|---|---|---|---|---|---|---|---|---|---|---|
| 5.35 | 0.39 | 0.29 | 0 | 0 | 1.27 | 5.02 | 2:1 | 180 | 900 | 62 | 93 | 58 | 37 |
| 5.35 | 0.39 | 0.29 | 0 | 0 | 1.27 | 5.02 | 3:1 | 180 | 900 | 43 | 90 | 39 | 25 |
| 5.36 | 0.40 | 0.29 | 0 | 0 | 1.52 | 5.01 | 2:1 | 180 | 900 | 42 | 93 | 39 | 25 |
| 5.36 | 0.40 | 0.29 | 0 | 0 | 1.52 | 5.01 | 3:1 | 180 | 900 | 56 | 97 | 53 | 35 |
| 5.35 | 0.39 | 0.29 | 0 | 0 | 1.27 | 5.02 | 3:1 | 180 | 900 | 73 | 89 | 66 | 42 |
| 5.36 | 0.40 | 0.29 | 0 | 0 | 1.52 | 5.01 | 3:1 | 180 | 900 | 77 | 89 | 69 | 44 |
| 5.33 | 0.29 | 0.29 | 0.07 | 0.05 | 1.26 | 5.03 | 3:1 | 180 | 600 | 47 | 83 | 39 | 25 |
| 5.35 | 0.29 | 0.30 | 0.07 | 0.05 | 1.50 | 5.04 | 3:1 | 180 | 600 | 42 | 83 | 34 | 22 |
| 5.33 | 0.29 | 0.29 | 0.07 | 0.05 | 1.26 | 5.03 | 3:1 | 180 | 900 | 87 | 94 | 81 | 52 |
| 5.35 | 0.29 | 0.30 | 0.07 | 0.05 | 1.50 | 5.04 | 3:1 | 180 | 900 | 87 | 96 | 83 | 54 |
| 5.35 | 0.29 | 0.30 | 0.07 | 0.05 | 1.50 | 5.04 | 3:1 | 170 | 600 | 34 | 82 | 28 | 18 |
| 5.35 | 0.29 | 0.30 | 0.07 | 0.05 | 1.50 | 5.04 | 3:1 | 170 | 1800 | 72 | 84 | 61 | 39 |

Example 7: Conversion of Sugar Stream 1837-A to Furfural

Furfural was produced and extracted into tetralin according to the methods described in Example 6. The feed was the CASE™ Xylose product, which is a C5 sugar product (i.e., sugar stream 1837-A), produced from bagasse in an industrial pilot campaign at Danville Va. PDU. Chemical analysis of the sugar stream 1837-A is provided herein (see Example 1).

The sugar was diluted with water. HCl and NaCl were added to give a final composition of: 6% DS (4.9% xylose), 1.5% HCl, 4.9% NaCl (all % wt/wt). The reaction was conducted at 180° C. and at a reaction residence time of 10 minute. The O:A ratio with the tetralin phase was 3.2. Xylose was converted to furfural at 58% and 68% selectivity, yielding 26% wt/wt furfural (40% molar yield).

Example 8: Continuous Distillation of Furfural

A stream of tetralin containing 0.85% wt/wt furfural, 0.04% wt/wt water, and 0.2% impurities is fed to a continuous fractional distillation column operating at a pressure of 75 mm Hg and a temperature of 40° C. A first distillation column performs a first distillation and is operated with a reflux condenser and a reboiler. According to an ASPEN Plus simulation, the column controls the distillate to a composition of about 78% wt/wt furfural, 18.5% wt/wt impurities, 3.5% wt/wt water, and 0.0014% wt/wt tetralin at 47.3° C. The bottom composition from the first distillation is 99.99% tetralin, 0.01% furfural, 100 ppm impurities, and 100 ppm water at 127.5° C. The bottom from the first distillation is returned for processing as recycled tetralin.

The distillate of the first distillation is fed to a continuous fractional distillation column operating at a pressure of 75 mmHg. The second distillation column performs a second distillation and is operated with a reflux condenser and a reboiler. According to an ASPEN Plus simulation, the column controls the remainder to 99.99% wt/wt furfural, 10 ppm water, 100 ppm tetralin, and 10 ppm impurities at 92.5° C. The second distillate comprises 4% wt/wt furfural, 80% wt/wt impurities, and 16% wt/wt water at 48° C. The bottom of the second distillation is taken as a purified product. The distillate of the second distillation is sent to waste.

Example 9: Furfural Product Composition

Furfural is isolated from tetralin by a multiple-stage distillation resulting in a furfural product comprising less than 5% teteralin and less than 5% water. The following molecules may be present at trace levels: formic acid, levulinic acid, acetic acid, 5-chloromethylfuran-2-carbaldehyde, 5,5'-diformyl-2,2'-difuran, HMF, and HCl.

Example 10: Tetralin Phase Composition

The tetralin phase after furfural distillation comprises residual furfural, water, HMF, HCl, NaCl, formic acid, levulinic acid, acetic acid, 5-chloromethylfuran-2-carbaldehyde, 5,5'-diformyl-2,2'-difuran,5-(furan-2-yl-hydroxymethoxymethyl)-furan-2-carbaldehyde, humins, and polyfurfural species.

Example 11: Hydrogenation of Furan to THF

Furan is dissolved in solvent and a hydrogenation catalyst is added. The reactor is flushed with nitrogen and hydrogen and pressurized. The reaction mixture is heated and stirred until the furan in the mixture is hydrogenated. The reactor is cooled with ice water before the reactor is opened. Samples are analyzed by GC to determine products. Greater than 90% furan is consumed in the course of the reaction and the major product is THF.

Example 12: A Large-Scale Continuous System for the Production of Furfural

A large-scale plant for the purpose of furfural production is designed according to the flow sheet of FIG. 3. An aqueous solution comprising a hemicellulose sugars stream 300 (e.g., stream 1837-A or 1836, 6% wt/wt, and 84.8 tons/day) enters the processing plant and is stored in Sugar mix tank 311. Sodium chloride (5% wt/wt) and HCl (1.5% wt/wt) are added to the solution. The hemicellulose sugars in the aqueous solution are 85% xylose wt/wt. Tetralin is stored in the solvent feed tank 341. Streams from each of the two tanks are flowed through heat exchange modules 312 and 342 (at 3.5 ton/hour aqueous and 10.6 ton/hour solvent) and mixed together inline to form a biphasic mixture (3:1 O:A wt/wt). The combined streams are passed through a plug flow reactor 313 and are heated to 356° F. for 900 seconds and controlled to a pressure of 1 bar above saturated steam pressure at 356° F. After conversion of at least 85% of the stream xylose to furfural, the mixture is cooled to 80° F. as it flows through a second heat exchange module 319A. Optionally, this stream can be interchanged to recover heat. The phases of the biphasic mixture are separated by decanter 344. The furfural-enriched organic stream is routed to a separator unit such as distillation unit 345, having a condensing module equipped with a reflux condenser. The solution is heated at a pressure of 70 Torr, and the furfural is distilled out of the solution. An overall isolated yield of pure furfural of greater than 80% (mol % from xylose) is achieved. The isolated furfural stream 344 is packaged for distribution or transferred directly for a sequential conversion to product. The condensed high boiling organic solvent (tetralin) form furfural-depleted organic stream 346 and remaining materials are recycled and HMF and other water-soluble impurities are washed off through an aqueous extraction at decanter 370. The tetralin is purified via centrifuge or decanter, and routed back to the solvent feed tank 341. The intermediate aqueous stream 350 from decanter 344 is pH adjusted to 3.5-5.5 and sent to an optional phase separation (e.g., MVR stripper 380) to produce an aqueous waste stream 381 and a stream containing less than 15% furfural that continues to centrifugal extractor (375), wherein furfural is extracted by a purified/return organic stream 373. The organic phase 390 from extractor 375 is returned to distillation 345 for furfural recovery. The furfural-depleted aqueous stream 376 from extractor 375 is sent to waste.

Example 13: An Alternative Large-Scale Continuous System for the Production of Furfural A large-scale plant for the purpose of furfural production is designed according to the flow sheet of FIG. 2. An aqueous solution comprising a hemicellulose sugars stream (e.g., stream 1837-A or 1836, 6% wt/wt, and 84.8 tons/day) enters the processing plant and is optionally evaporated to 20-80% wt/w. The stream is blended into dilution tank 111. A recycled aqueous stream is continuously added to dilution tank 111 and maintains a sugar concentration of 6% wt/wt in the dilution tank 111. Sodium chloride and HCl are added to dilution tank 111 as needed in order to maintain 5% wt/wt salt and 1.5% wt/wt HCl. Tetralin is stored in the solvent feed tank 141. An organic stream 204 from the solvent feed tank 141 is continuously flowed through a preheat heat exchanger at 392° F. and then mixed with an aqueous sugar stream 202 from the distillation tank at approximately 140° F. The combined stream is flowed through a heat exchanger (not pictured) at 356° F. Optionally, this heat exchanger is interchanged with another process stream to recover heat. The combined streams are passed through a plug flow reactor 113 for between 600 and 1800 seconds. The stream is then passed through a cooling heat exchanger 119A at 80° F. The cooled stream (i.e., biphasic reaction mixture 206) is then filtered (filter 120) and sent to phase separation 144 (e.g., a centrifuge or decanter). The furfural-enriched organic stream 208 is sent to a separator unit 145 (e.g., a distillation column). Furfural is separated from the organic stream and collected as an isolated furfural stream 230. The furfural-depleted organic stream 212 exits distillation and is optionally mixed with water to recover HMF in phase separation 175. The organic stream is then recycled back to solvent feed tank 141. A portion of the organic stream from distillation is directed to phase separation 175, wherein it is mixed with a basic aqueous stream at a pH of 10 or greater. The mixed stream is either centrifuged or decanted. The organic stream blends back with the organic recycle to the solvent feed tank 141. The aqueous waste stream 176 exits as water to waste. A portion of the organic phase from the separator unit 145 (e.g., distillation unit) is directed to phase separation 175, wherein it is mixed with the intermediate aqueous stream 210 from phase separation 144. When mixed, the organic phase extracts residual furfural from the aqueous phase. The streams are centrifuged or decanted after mixing. Once separated, the organic phase is directed to separator unit 145 for furfural recovery via, e.g., distillation. The aqueous phase from phase separation 175 is directed back to dilution tank 111 for recycling of sugars, HCl, and salt. A purge stream is taken from that aqueous stream, which exits as waste. The volume of the waste stream is tied to the concentration target for the inlet stream evaporator. Waste is purged to balance process water accumulation caused by inlet dilution.

Example 14: Conversion of Arabinose to Furfural

A reaction stock solution was made which contained 6.10% w/w arabinose, 4.98% w/w NaCl, and 1.55% w/w HCl. This stock solution was mixed with tetralin in an O:A ratio of 2.99 in a pressure reaction tube. The capped tube was placed in an oil bath at 180° C. and stirred for ten minutes. The reactions was cooled in an ice bath then separated in a centrifuge. The aqueous phase was analyzed by HPLC and the organic phase was analyzed by GC. The analyses showed 40% conversion of arabinose to furfural, at selectivity of 70%, yielding 17% furfural (wt/wt) or 28% (molar yield).

What is claimed is:

1. A system for producing furfural, wherein the system is configured to produce at least 1.0 ton of furfural for each 2.3 tons of hemicellulose sugars provided, wherein the hemicellulose sugars comprise at least 80% xylose (by weight), wherein the system is configured to catalytically reduce furfural using a dissolved acid catalyst, and wherein the system is configured for processing at least 1.1 tons of hemicellulose sugars per day.

2. The system of claim 1, wherein the hemicellulose sugars comprise at least 1 C6 sugar selected from the group consisting of glucose, mannose, and galactose.

3. The system of claim 1, wherein the hemicellulose sugars further comprise arabinose.

4. The system of claim 1, wherein the hemicellulose sugars comprise at least 90% xylose (wt/wt).

5. The system of claim 1, further comprising a reaction control unit configured to adjust temperature or reaction residence time in a reactor based on chemical composition of the hemicellulose sugars.

6. The system of claim 1, further comprising a dilution control unit that controls:
  a) an amount or a concentration of an acid and a salt in an aqueous sugar stream;
  b) a concentration of the hemicellulose sugars in the aqueous sugar stream, and
  c) an amount of purge water released from the system.

7. The system of claim 6, wherein the dilution control unit adjusts the salt concentration in the aqueous sugar stream to about 5% (wt/wt).

8. The system of claim 6, wherein the dilution control unit adjusts the-concentration of the hemicellulose sugars in the aqueous sugar stream to 2-10% (wt/wt).

9. The system of claim 6, wherein the system comprises a dilution tank operably connected to the dilution control unit and a furfural-depleted aqueous stream from a separation module of the system, and wherein the furfural-depleted aqueous stream comprises water, acid and salt.

10. The system of claim 1, wherein the system comprises an extraction module for extracting hydrophilic impurities from an organic phase solvent by contacting in a counter current mode with an aqueous phase comprising acid and salt.

11. The system of claim 1, wherein the system is configured to recycle at least 60% of a furfural-depleted aqueous solution.

12. The system of claim 1, wherein the system comprises a preheating unit for preheating an organic solvent and an output to transfer the organic solvent to a reactor.

13. The system of claim 1, wherein the system comprises a separation module, wherein the separation module is configured for separating furfural, an aqueous stream, and an organic solvent stream.

14. The system of claim 1, wherein the system comprises a solvent feed tank, a dilution feed tank, a reactor downstream of the solvent feed tank and the dilution feed tank, and a separation module downstream of the reactor; wherein the separation module is configured for separating furfural, an aqueous stream, and an organic solvent stream; wherein (i) the solvent feed tank is configured to preheat solvent separated by and exiting from the separation module; (ii) the dilution feed tank is configured to dilute the hemicellulose sugars with the aqueous stream separated by and exiting from the separation module; and (iii) the reactor is configured to maintain the preheated solvent and the diluted hemicellulose sugars at a set temperature and pressure thereby converting xylose from the hemicellulose sugars into furfural.

15. The system of claim 14, wherein the separation module comprises one or more distillation columns.

16. The system of claim 1, wherein the system is operable on a continuous basis.

17. The system of claim 1, comprising an aqueous solution recycling loop and an organic solvent recycling loop.

18. The system of claim 1, wherein the system comprises a separation module for separating a reaction mixture into a furfural-enriched product stream, an aqueous stream and an organic solvent stream, wherein (i) the furfural-enriched product stream has a furfural purity of at least 90%; (ii) the aqueous stream comprises acid and less than 1% (wt/wt) organic solvent and less than 2% (wt/wt) hemicellulose sugars; and (iii) the organic solvent stream comprises an S5 solvent and less than 1% (wt/wt) non-S5 solvent impurities.

* * * * *